United States Patent [19]

Nelson

[11] Patent Number: 6,093,541
[45] Date of Patent: *Jul. 25, 2000

[54] MASS SPECTROMETER HAVING A DERIVATIZED SAMPLE PRESENTATION APPARATUS

[75] Inventor: Randall W. Nelson, Phoenix, Ariz.

[73] Assignee: Arizona State University Board of Regents, Tempe, Ariz.

[*] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/781,110

[22] Filed: Jan. 9, 1997

Related U.S. Application Data

[63] Continuation of application No. 08/477,107, Jun. 7, 1995, abandoned.

[51] Int. Cl.[7] ...................................................... C12Q 1/68
[52] U.S. Cl. .................................. 435/6; 435/23; 435/24
[58] Field of Search .................................. 435/6, 23, 24, 435/174, 281; 250/288, 423 P; 313/566

[56] References Cited

U.S. PATENT DOCUMENTS 4,988,879  1/1991  Zare et al. ........................... 250/423 P

FOREIGN PATENT DOCUMENTS

WO 94/28418  12/1994  WIPO .

OTHER PUBLICATIONS

Dogruel, D., Rapid Tryptic Mapping using Enzymatically Active Mass Spectrometer Probe Tips, Anal Chem 67(23) 4343–4348, Dec. 1995.

Eugenii Yu. Katz, "A Chemically Modified Electrode Capable of a Spontaneous Immobilization of Amino Compounds Due to its Functionalization with Succinimidyl Groups," J. Electroanal. Chem., 291, pp. 257–260 (1990).

Pierce Corporation Catalog, "Cross–Linking," pp. T–155 to T–200 (1995).

Nelson et al., Mass Spectrometric Immunoassay, Analytical Chemistry, 34:1153–1158, (Apr. 1, 1995).

*Primary Examiner*—Ralph Gitomer
*Attorney, Agent, or Firm*—Baker Botts L.L.P.

[57] ABSTRACT

A mass spectrometer having a derivatized sample presentation apparatus is provided. The sample presentation apparatus has a complex bound to the surface of the sample presentation apparatus. This complex includes a molecule which may chemically modify a biomolecule.

10 Claims, 25 Drawing Sheets

Residues of lysozyme following 10 minute digest on an Au/trypsin probe tip

| Mass (observed) Da | Mass (calculated) Da | ΔDa | Residues |
| --- | --- | --- | --- |
| 936.6 | 937.02 | −0.42 | 62−68 |
| 1046 | 1045.54 | 0.46 | 117−125 |
| 1277.4 | 1276.64 | 0.76 | 22−33 |
| 1424.8 | 1424.78 | 0.02 | 1−13 |
| 1429.6 | 1428.64 | 0.96 | 34−45 |
| 1435.5 | 1434.63 | 0.87 | 62−73 |
| 1475.8 | 1474.75 | 1.05 | 117−129 |
| 1548 | 1546.78 | 1.22 | 113−125 |
| 1581 | 1580.96 | 0.04 | 1−14 |
| 1677.1 | 1676.90 | 0.20 | 98−112 |
| 1707.2 | 1707.04 | 0.16 | 115−129 |
| 1755 | 1754.86 | 0.14 | 46−61 |
| 1805.4 | 1805.08 | 0.32 | 97−112 |
| 1947.5 | 1947.19 | 0.31 | 98−114 |
| 1977.8 | 1977.33 | 0.47 | 113−129 |
| 2076.1 | 2075.37 | 0.73 | 97−114 |
| 2126 | 2125.38 | 0.62 | 15−33 |
| 2281.7 | 2281.57 | 0.13 | 14−33 |
| 2306.9 | 2304.69 | 2.21 | 97−116 |
| 2339.2 | 2336.72 | 2.48 | 74−96 |
| 2437.1 | 2436.88 | 0.22 | 1−21 |
| 2467.4 | 2464.90 | 2.50 | 74−97 |
| 2680.8 | 2679.94 | 0.86 | 22−45 |
| 3172.4 | 3171.41 | 0.99 | 46−73 |
| 3334.8 | 3333.84 | 0.96 | 97−125 |
| 3537.2 | 3535.68 | 1.52 | 15−45 |
| 3689.9 | 3692.05 | −2.15 | 14−45 |
| 3754.4 | 3751.26 | 3.14 | 62−96 |
| 4125.5 | 4122.78 | 2.72 | 74−112 |
| 4418.4 | 4415.79 | 2.61 | 74−114 |
| 5098 | 5097.81 | 0.19 | 1−45 |
| 5273 | 5271.70 | 1.30 | 15−61 |
| 5488.3 | 5487.10 | 1.20 | 46−96 |

FIG.2

Residues of lysozyme following 10 minute digest of
1 pmol with free-trypsin and agarose-immobilized trypsin.

| Free Trypsin Mass (observed) Da | Immobilized Trypsin Mass (observed) Da | Residues | Autolysis Product |
|---|---|---|---|
| 935.3 | 936.5 | 62-68 | |
| 1046.1 | 1046.1 | 117-125 | |
| 1176.7 | | | x |
| 1277.4 | 1276.9 | 115-125 | |
| 1435.6 | 1434.9 | 62-73 | |
| 1458.9 | | | x |
| 1476.9 | | 117-129 | |
| 1497.9 | | | x |
| 1548.8 | | 13-125 | |
| 1582.4 | 1581.8 | 1-14 | |
| 1678.2 | 1677.6 | 98-112 | |
| 1709.4 | | 115-129 | |
| 1756.7 | 1755.5 | 46-61 | |
| 1806.4 | 1805.8 | 97-112 | |
| 2166 | 2164.4 | | x |
| 2190.6 | | | x |
| 2274 | 2274.8 | | |
| 2471.5 | | | x |
| 3168 | | 46-73 | |
| 3227.9 | | | x |
| 3372.5 | 3371.1 | | x |

α-cobratoxin

α-cobratoxin -30 minute digest on "active" Au/trypsin probe (DTT present)

RELATIVE INTENSITY vs m/z

FIG. 11

α-cobratoxin −30 minute digest on "active" Au/trypsin probe (DTT present)

hPTH Au/α-chymotrypsin/Carboxypeptidase P

| Endopeptidase Signal | Ladder Signal | Difference | Residue | Error |
|---|---|---|---|---|
| 2,738.7 | 2,738.9 | 0 | | |
| | 2,552.4 | 186.5 | W | +0.3 |
| | 2,423.5 | 128.9 | E | −0.2 |
| | 2,324.3 | 99.2 | V | +0.1 |
| | 2,168.1 | 156.2 | R | 0.0 |
| | 2,038.8 | 129.3 | E | +0.2 |
| | 1,907.6 | 131.2 | M | 0.0 |
| 1,850.0 | | | | |
| | 1,820.6 | 87.0 | S | −0.1 |
| 1,706.2 | | | | |
| 1,398.5 | | | | |

FIG. 15 hPTH Au/trypsin/Carboxypeptidase P (* Denotes Lys-Lys)

| Endopeptidase Signal | Ladder Signal | Difference | Residue | Error |
|---|---|---|---|---|
| *3,264.3 | | | | |
| *3,136.1 | 3,136.1 | 128.2 | K | 0.0 |
| *3,007.9 | 3,007.8 | 128.3 | K | +0.1 |
| | 2,851.8 | 156.0 | R | −0.2 |
| | 2,738.6 | 113.2 | L/I | 0.0 |
| | 2,552.4 | 186.2 | W | 0.0 |
| | 2,423.5 | 128.9 | E | −0.2 |
| 2,323.8 | 2,324.0 | 99.5 | V | +0.4 |
| | 2,167.8 | 156.2 | R | 0.0 |
| | 2,038.5 | 129.3 | E | +0.2 |
| | 1,907.4 | 131.1 | M | 0.0 |
| | 1,820.3 | 87.1 | S | 0.0 |
| | 1,706.3 | 114.0 | N | −0.1 |
| 1,698.2 | | | | |
| 1,570.0 | | 128.2 | K | 0.0 |
| 1,455.9 | | | | |
| *1,128.7 | | | | |
| *1,000.5 | | 128.2 | K | 0.0 |
| 886.4 | | | | |
| *872.3 | | 128.2 | K | 0.0 |
| 830.4 | | | | |
| 702.3 | | 128.1 | K | −0.1 |

FIG. 19

MASS SPECTROMETER HAVING A DERIVATIZED SAMPLE PRESENTATION APPARATUS

This application is a continuation of application Ser. No. 08/477,107 filed on Jun. 7, 1995, now abandoned.

This invention was made in whole or in part with funds from the United States Government under a contract awarded by the U.S. Departement of Energy. The U.S. Government has certain rights in this invention in accordance with the terms of the contract.

BACKGROUND OF THE INVENTION

The present invention relates generally to derivatized mass spectrometry sample presentation apparatuses, and more specifically, to mass spectrometry sample presentation apparatuses derivatized with complexes including at least one molecule which modifies a biomolecule.

Conventionally, mass spectrometry is a technique used to characterize analytes by determining their molecular weight. Ordinarily, mass spectrometry involves the steps of: coating a sample presentation apparatus with an analyte, introducing the sample presentation apparatus into the mass spectrometer, volatilizing and ionizing the analyte, accelerating the ionized analyte toward a detector by exposing the ions to an electric and/or a magnetic field, and analyzing the data to determine the mass to charge ratio of specific analyte ions.

If an analyte remains intact throughout this process, data will be obtained which corresponds to a molecular weight for the entire intact analyte ion. Typically however, it is beneficial to additionally obtain data corresponding to the molecular weight of various fragments of the analyte. It is also beneficial to obtain data which only corresponds to the pure analyte, even when impurities are present. Therefore, it is advantageous to be able to modify analytes by purifying and/or cleaving them, prior to determining their molecule weight.

In conventional mass spectrometry, the analyte is either modified before it is coated on the sample presentation apparatus, or during the volatilization and ionization steps, which occur inside the mass spectrometer. It is known that biomolecules (e.g. polypeptides, deoxyribonucleic acid (DNA), ribonucleic acid (RNA), or carbohydrates) can be selectively digested at specific locations by exposing them to immobilized complexes. However, it is disadvantageous to modify an analyte before it is coated on the sample presentation apparatus, as this extra step slows the overall process, involves loss of the analyte, and can possibly introduce contaminants. Moreover, if the fragments are generated in solution in a reaction between the analyte and a reagent, the kinetics of the reaction may be rather slow, thus adding further delay. It is also disadvantageous to generate fragments during the volatilization and ionization steps as such methods typically provide little control over the analyte cleavage site and may lead to excessive degradation of the analyte.

It is further known to use the Matrix-Assisted Laser Desorption/Ionization ("MALDI") technique to volatilize and ionize biomolecules in a mass spectrometer. This technique involves surrounding a biomolecule in a special matrix material. A LASER beam, tuned to a frequency where the matrix absorbs, is targeted on the matrix material. The LASER transfers sufficient energy to volatilize a small portion of the matrix material. A small number of analyte molecules are thus carried along with the matrix material into the vapor phase in the mass spectrometer.

Prior to the development of MALDI, analysis of biomolecules by mass spectrometry was quite difficult, if not impossible, since no techniques were available which were gentle enough to volatilize intact biomolecules without any degradation or fragmentation. While the MALDI technique provides an advantageous technique for volatilizing biomolecules, this technique does not provide for generation of analyte fragments or purification of an analyte prior to introducing the analyte onto a sample presentation apparatus. In particular, the need for extra fragmentation or purification steps slow the overall process, wastes valuable analyte, and can introduce contaminants.

It is known from PCT Publication No. 94/28418 to use a sample presentation apparatus for laser desorption and ionization mass spectrometry, wherein the sample presentation apparatus is derivatized with surface associated molecules for promoting desorption and ionization of biomolecules. In such surface-bound biomolecule methods, the surface associated molecules bind biomolecules, and later promote desorption of the biomolecules when they are exposed to LASER radiation. Biomolecule fragments are generated by exposing the surface-bound biomolecules to reagents in solution, and later washing away the reagent. This procedure is problematic because it can introduce contaminants, which reduces the quality of the collected data. Specifically, if any reagent is left on the surface after the washing procedure, it will be the first material to be volatilized by the LASER beam, and may very well swamp the signals from the material of interest, thereby adversely affecting the data.

Moreover, such a process is difficult because it relies on new and unproven systems for volatilizing biomolecules. In contrast, MALDI matrix systems are well studied, and known to effectively and gently volatilize biomolecules. MALDI matrices cannot be used with the surface-associated molecule method because the matrix covers the surface-bound biomolecules, and thus would completely prevent the acquisition of useful data.

Furthermore, it is also disadvantageous to directly bind biomolecules to a sample presentation surface, because this would eliminate the possibility of transferring a modified biomolecule to a second region on the presentation surface or a second presentation surface, where it could be exposed to other modifying reagents. Therefore, any chemical reactions according to the surface-bound analyte method, must be performed sequentially, rather than in parallel. In such sequential methods, the bound analyte must be reacted with one reagent, introduced into the mass spectrometer, removed, and then subsequently reacted with a second reagent. Each of these steps is disadvantageous as it presents an opportunity for contaminating the sample and introduces further delay.

For the foregoing reasons, there is a need for a mass spectrometry sample presentation apparatus which provides a rapid, efficient method for analyzing biomolecules using proven, advantageous MALDI matrices.

SUMMARY OF THE INVENTION

Accordingly, it is an object of the invention to provide a sample presentation apparatus, mass spectrometry method, and mass spectrometer that overcome the disadvantages of the prior art.

Another object of the invention is to provide an improved sample presentation apparatus including a complex capable of modifying biomolecules wherein it is unnecessary to separate any reagent from the modified biomolecule to prevent contaminating data obtained from the modified biomolecule.

Another object of the invention is to provide an improved derivatized mass spectrometry sample presentation apparatus which minimizes sample loss, and thus works effectively with extremely small amounts of biomolecules.

Yet another object of the invention is to provide a mass spectrometry sample presentation apparatus which presents a complex capable of chemically modifying a biomolecule in a high effective concentration, and thus increases the rate of biomolecule modification reactions.

Another object of the invention is to provide a mass spectrometry sample presentation apparatus which digests and/or purifies biomolecules.

A further object of the invention is to provide a derivatized mass spectrometry sample presentation apparatus which can utilize existing optimized MALDI matrix systems.

Another object of the invention is to provide a mass spectrometry method wherein biomolecules are reacted with one reagent, and then a portion of the reacted biomolecules are reacted with a different reagent.

A further object of the invention is to provide a method for making a mass spectrometry sample presentation apparatus which overcomes the disadvantages of the prior art.

Yet another object of the invention is to provide a method of analyzing a biomolecule, wherein the biomolecule is exposed to the derivatized surface of the sample presentation apparatus and then incubated in a moist atmosphere. Subsequently, a MALDI matrix material is added, and finally the sample presentation apparatus is introduced into the mass spectrometer.

Another object of the invention is to provide a method of analyzing a polypeptide, wherein the molecular weight data is used to determine a limited amino acid sequence of the peptide. The limited amino acid sequence obtained by this method can then be used to generate corresponding nucleic acid sequences. These nucleic acid sequences can then be used to search a computer database containing known nucleic acid sequences. A match may identify a known nucleic acid sequence which codes for the polypeptide.

A further object of the invention is to provide an improved mass spectrometer which incorporates an improved mass spectrometry sample presentation apparatus.

These and other objects of the present invention are obtained by providing a mass spectrometry sample presentation apparatus comprising a mass spectrometry sample presentation surface, wherein a complex is bound to the surface which includes at least one molecule which chemically modifies a biomolecule.

A method of making a sample presentation apparatus is further provided wherein a complex, which includes at least one molecule which chemically modifies a biomolecule, is bound to the sample presentation apparatus surface.

The objects of the present invention are further accomplished through a method of analyzing a biomolecule comprising the steps of:

(a) providing a mass spectrometry sample presentation surface;

(b) binding at least one complex to the surface wherein the complex includes at least one molecule which chemically modifies a biomolecule;

(c) contacting the biomolecule with the surface, thereby chemically modifying the biomolecule; and (d) determining the molecular weight of the chemically modified biomolecule in a mass spectrometer.

The objects of the present invention are further obtained by a mass spectrometer. The mass spectrometer has a sample presentation surface with a surface-bound complex including at least one molecule which chemically modifies a biomolecule. The mass spectrometer also has a vacuum interlocking device for introducing the surface into the machine, an apparatus for volatilizing and ionizing the chemically modified biomolecule, an electric field generator, a detector and electronics for determining the molecular weight to charge ratio of the modified biomolecule ions.

The sample presentation apparatus, method of making a sample presentation apparatus, method of analyzing biomolecules and mass spectrometer of the present invention provide mass spectrometry information for biomolecules which is both easier to obtain and of higher quality, than was previously possible.

BRIEF DESCRIPTION OF THE DRAWINGS

FIG. 2 is a summary illustrating the correlation between the calculated and observed masses for chicken egg lysozyme fragments.

FIG. 6 is a summary of the residues of 1 picomole of chicken egg lysozyme obtained following a 10 minute digest with free trypsin and agarose-immobilized trypsin.

Figure 8:
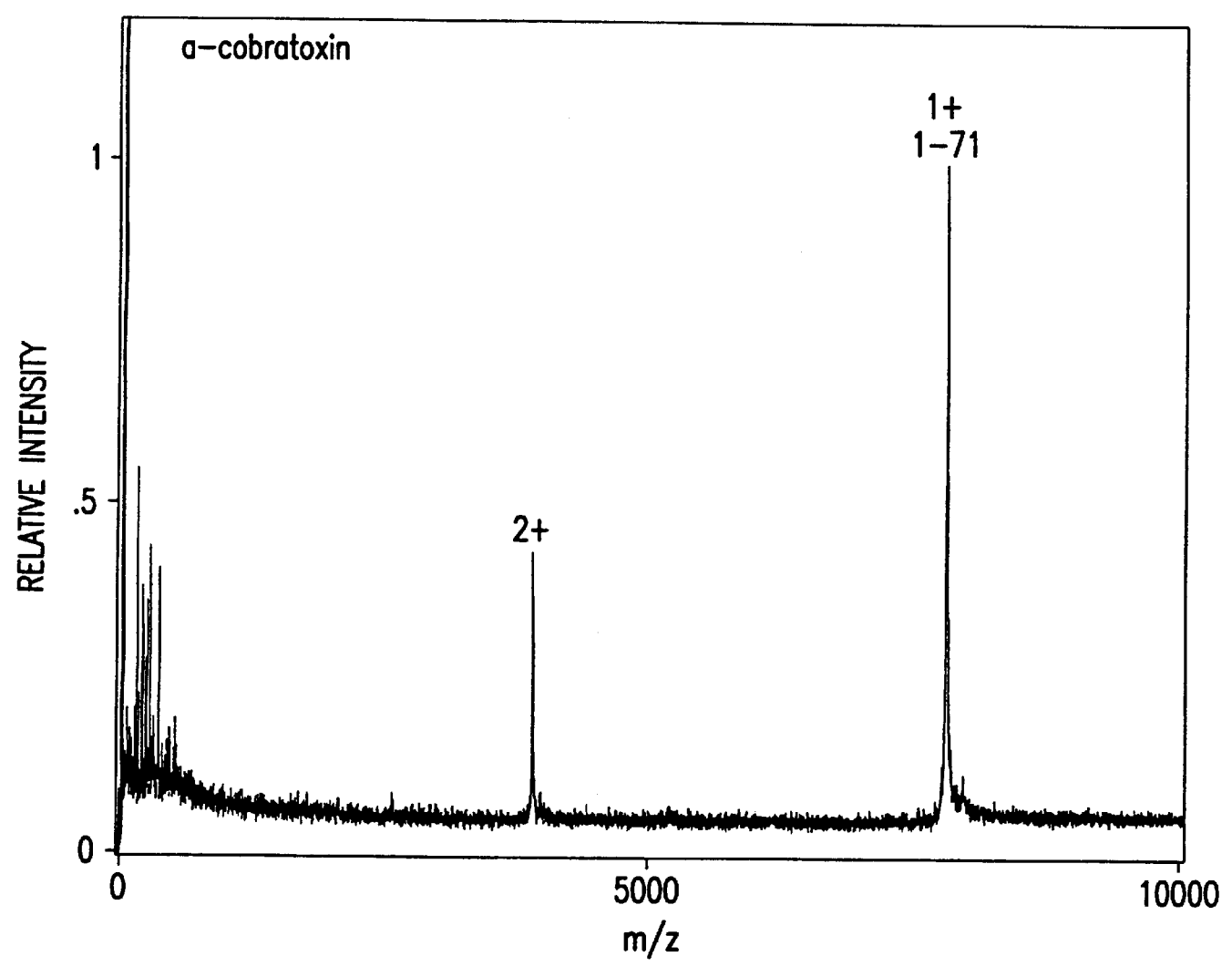

FIG. 8 is a MALDI mass spectrum of undigested α-cobratoxin.

FIG. 10 is a MALDI mass spectrum of approximately 10 picomoles of α-cobratoxin digested for 30 minutes with a surface-bound trypsin sample presentation apparatus in the presence of a reducing agent.

FIG. 11 is an exploded view of the MALDI mass spectrum of FIG. 10 in the m/z range of 1,000–5,000 Pa.

FIG. 15 illustrates the partial peptide sequence of hPTH generated by analyzing the mass spectrometry data from α-chymotrypsin and α-chymotrypsin/carboxypeptidase P (cpp) fragments.

FIG. 19 is an overlay of the mass spectra of trypsin and trypsin/cpp fragments illustrating the use of both the large-scale and ladder information to extend the sequence determination.

DESCRIPTION OF THE PREFERRED EMBODIMENTS

Figure 1:
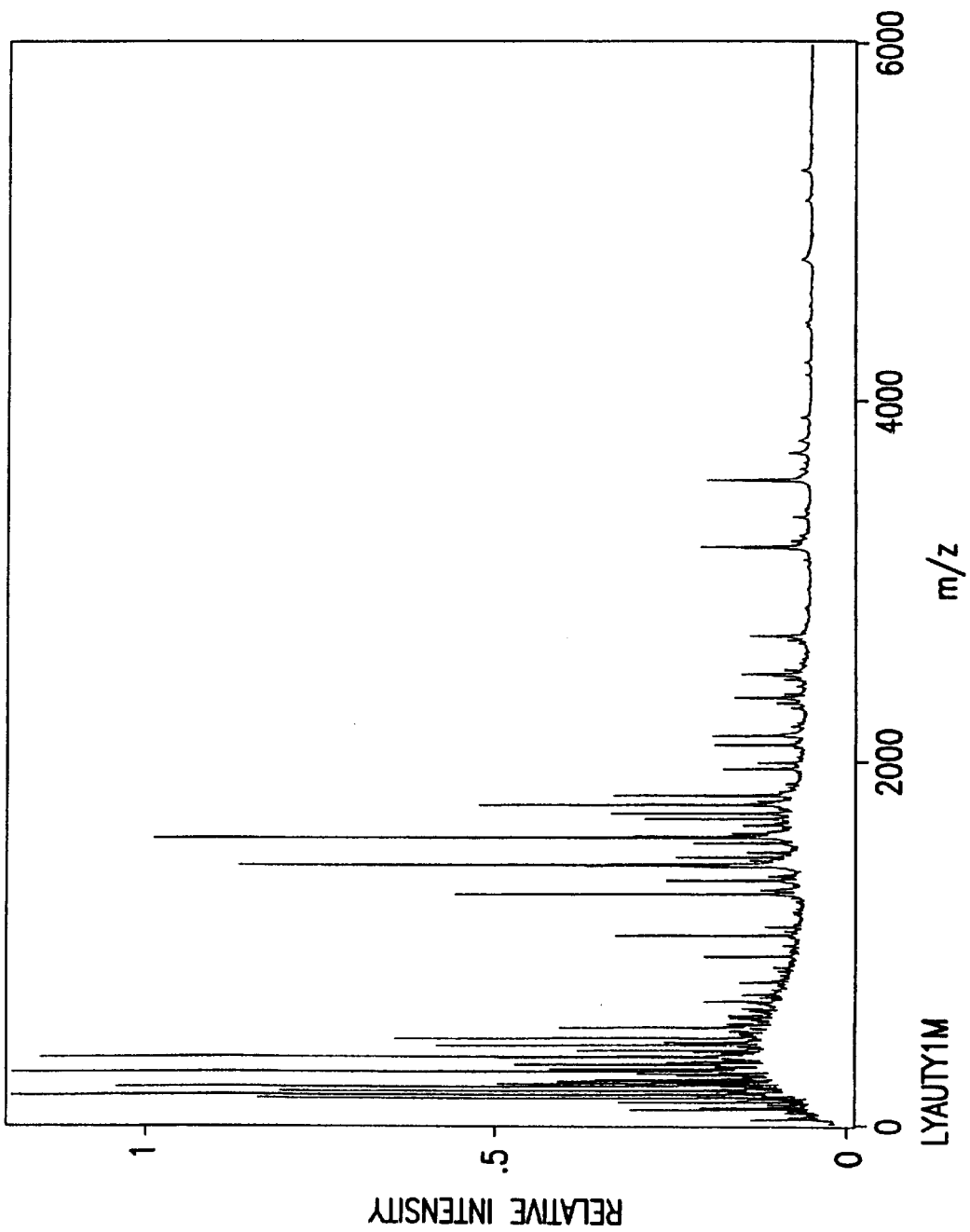
FIG. 1 is a MALDI mass spectrum of 10 picomoles of chicken egg lysozyme digested for 10 minutes with surface-bound trypsin.

The present invention provides a conventional mass spectrometry sample presentation apparatus which has a surface derivatized with complexes which chemically modify biomolecules. This apparatus is typically exposed to a biomolecule, and incubated to allow the complex to modify the biomolecule. After incubation, the modified biomolecule is preferably surrounded with a MALDI matrix material and then introduced into a mass spectrometer. The invention also include further embodiments such as a mass spectrometer incorporating such a sample presentation apparatus. Further embodiments provide a method of performing mass spectrometry, and of making a sample presentation apparatus.

As used herein, the term "derivatized" is meant to refer to a mass spectrometry sample presentation apparatus having a bound complex. A derivatized sample presentation apparatus in accordance with the invention may be composed of any suitable material. The material can be a solid or liquid. Suitable solid materials include, but are not limited to insulators such as quartz, semiconductors such as doped silicon and the like, and conductors including metals such as steel, gold and the like. Various insulating or conductive polymers may also be used. The surface of the sample presentation apparatus need not be made of the same material as the rest of the apparatus. It is preferable for the surface to be clean so that a complex may adhere to the surface.

The complex attached to the presentation apparatus surface has two distinct functionalities. As used herein, the term "complex" refers to a chemical which includes at least one molecule which chemically modifies a biomolecule. The complex has a "tethering" function, wherein it is capable of attaching itself at at least one end to the surface. Moreover, it also has a "reactive" function wherein it is capable of chemically modifying the analyte. As used herein, the term "chemically modify" is meant to refer to purification or digestion of an analyte, but not binding an analyte. The complex may further comprise a tethering molecule which binds to the surface, and a reactive molecule which binds to the tethering molecule and modifies a biomolecule.

Typically, the "tethering" function is associated with one group of atoms (i.e., the tethering molecule) while the "reactive" function is associated with a different group of atoms (i.e., the reactive molecule). The complex may comprise both a tethering molecule which binds to the sample presentation surface and a reactive molecule which binds to the tethering molecule and modifies a biomolecule. However this separation of function is not necessary. The tethering molecule is preferably selected from the class of molecules which has proven to be effective as an immobilized ligand. Many specific examples of such molecules are listed on pages T-156 to T-200 of the 1995 Pierce Corporation Catalog (Pierce Corp., P.O. Box 117, Rockford Ill. 61105). Suitable tethering molecules include: dithiothreitol, dimethyladipimidate-2*HCL, dimethylpimelimidate*HCL, dimethylsuberimidate*2HCL, dimethyl 3,3-dithiobispropionimidate*2HCL, disuccinimidyl glutarate, disuccinimidyl suberate, bis (sulfosuccinimidyl) suberate, dithiobis(succinimidylpropionate), dithiobis (sulfosuccinimidylpropionate), ethylene glycobis (succinimidylsuccinate), ethylene glycobis (sulfosuccinimidylsuccinate), disuccinimidyl tartarate, disulfosuccinimidyl tartarate, bis[2-(succinimidyloxycarbonyloxy)ethyl]sulfone, bis[2-(sulfosuccinimidooxy-carbonyloxy)ethyl]sulfone, succinimidyl 4-(N-maleimido-matyl) cyclohexane-1-carboxylate, sulfo-succinimidyl 4-(N-maleimidomethyl) cyclohexane-1-carboxylare, m-Maleimidobenzoyl-N-hydroxysuccinimide ester, m-maleimidobenzoyl-N-hydroxysulfosuccinimide ester, succinimidyl 4-p-maleimido-phenyl)-butyrate, sulfosuccinimidyl 4-(p-maleimidophenyl)-butyrate, bismaleimidohexane, N-(λ-maleimidobutyryloxy)succinimide ester, N-(λ-maleimidobutyryloxy)sulfosuccinimide ester, n-succinimidyl(4-iodoacetyl)aminobenzoate, sulfosuccinimidyl(4-iodoacetyl)-aminobenzoate, 1,4-di-[3'-2'-pyridyldithio(propionamido)butane], 4-succinimidyl-oxycarbonyl-α(s-pyridyldithio)toluene, sulfosuccinimidyl-6-[α-methyl-α-(2-pyridyldithio)-toluamido]hexanoate, n-succinimidyl-3(2-pyridyldithio)-propionate, succinimidyl 6-[3-(2-pyridyldithio)-propionamido]hexanoate, sulfosuccinimidyl-6-[-3-(2-pyridyldithio)-propionamido] hexanoate, sulfosuccinimidyl-6-[3-(2-pyridyldithio)-propionamido]hexanoate, 3-(2-pyridyldithio)-propionyl hydrazine, 1-ethyl-3-(3-dimethylaminopropyl)-carbodiimide hydrochloride, n,n'-dicyclohexylcarbodiimide, 4-(p-azidosalicylamido)-butylamine, azidobenzoyl hydrazine, N-5-azido-2-nitrobenzoyloxysuccinimide, n-5-azido-2-nitrobenzoyloxysuccinimide, n-[4-(p-azidosalicylamido)butyl]-3'(2'-pyridyldithio)propionamide, p-azidophenyl glyoxal monohydrate, 4-(p-azidosalicyl-amido)butylamine, 1-(p-azidosalicylamido)-4-(iodoacetamido)butane, bis-[β-4-azidosalicylamido)ethyl] disulfide, n-hydroxysuccinimidyl-4-azidobenzoate, n-hydroxysulfo-succinimidyl 4-azidobenzoate, n-hydroxysuccinimidyl-4-azidosalicylic acid, n-hydroxysulfosuccinimidyl-4-azidosalicylic acid, sulfosuccinimidyl-(4-azidosalicylamido)-hexanoate, p-nitrophenyl-2-diazo-3,3,3-trifluoropropionate, 2-diazo-3, 3,3,-trifluoro-propionate, n-succinimidyl-(4-azidophenyl)1, 3'/-dithiopropionate, sulfosuccinimidyl-(4-azidophenyldithio)propionate, sulfosuccinimidyl-2-(7-azido-4-methylcoumarin-3-acetoamide)ethyl-1,3'- dithiopropionate, sulfosuccinimidyl 7-azido-4-metylcoumarin-3-acetate, sulfosuccinimidyl 2-(m-azido-o-nitrobenzamido)-ethyl-1,3'-dithiopropionate, n-succeinimidyl-6-(4'-azido-2'-nitrophenyl-amino) hexanoate, sulfosuccinimidyl 6-(4'-azido-2'-nitrophenylamino)hexanoate, sulfosuccinimidyl 2-(p-azidosalicylamido)ethyl-1,3'-dithiopropionate, sulfosuccinimidyl 4-(p-azidophenyl)-butyrate. Various protocols for using such ligands are explained in "Immobilized Affinity Ligand Techniques" by Greg T. Hemanson et al. (1992), which is incorporated herein by reference.

The complex may chemically modify a biomolecule analyte in several different ways. As used herein, the term "biomolecule" is meant to refer to DNA, RNA, polypeptides, carbohydrates and combinations thereof. For example, the complex may digest, or purify the biomolecule. As used herein, the term "digest" is meant to refer to chemical or enzymatic cleavage of a biomolecule into fragments and the term "purify" means to remove undesirable materials from a solution containing the biomolecule. As used herein, the term "fragment" is meant to refer to a part of a biomolecule which has been cleaved from the rest of the biomolecule using a chemical or enzymatic reagent. Several different reactive molecules are available for digesting biomolecules. If the biomolecule is a polypeptide, the complex will preferably comprise a chemical cleavage agent or an enzymatic protease.

Enzymatic proteases are specific polypeptides which cleave polypeptides. Proteases may cleave themselves by a process known as autolysis. Several enzymatic proteases cleave polypeptides between specific amino acid residues. Examples of proteases which cleave nonspecifically include subtilisin, papain and thermolysin. Examples of proteases which cleave at least somewhat specifically include: aminopeptidase-M, carboxypeptidase-A, carboxypeptidase-P, carboxypeptidase-B, carboxypeptidase-Y, chymotrypsin, clostripain, trypsin, elastase, endoproteinase Arg-C, endoproteinase Glu-C, endoproteinase Lys-C, factor Xa, ficin, pepsin, plasmin, staphylococcus aureus V8 protease, proteinkinase K and thrombin.

Chemical cleavage agents which cleave polypeptides between specific amino acid residues include cyanogen bromide, O-iodosobenzoate or O-iodosobenzoic acid, dilute hydrochloric acid, N-bromosuccinimide, sodium hydrazine, lithium aluminum hydride, hydroxylamine and 2-nitro-5-thiocyanobenzoate. Suitable chemical cleavage agents also include Sanger's Reagent (2,4-dinitrofluorobenzene), Edmund's Reagent (Phenylisothiocyanate), and immobilized derivatives of these Reagents. Moreover, coordinated transition metal complexes such as the tetradentate Co (III) complex, β-[Co (triethylenetetramine)—OH($H_2O$)], may also be used as effective cleavage agents. See Buckingham et al. 89 J.A.C.S. 1082 (1967).

When the biomolecule to be analyzed is a polypeptide, it may be advantageous to add a reducing agent to sever any disulfide bonds between the amino acids. Severing these bonds will result in further fragmentation of the peptide, thus yielding more information about peptide structure. Disulfide reduction agents may be bound onto the sample presentation surface, or used in solution. Suitable disulfide reducing agents include β-mercaptoethanol, cysteine, and dithiothreitol (DTT). Carboxypeptidase-P, dithioerythritol (DTE) lipomide and N-acetylhomocysteine can be used as surface-bound disulfide reduction agents.

For biomolecules such as DNA or RNA, it may be advantageous to add a restriction endonuclease or exonuclease to the sample presentation apparatus surface. These enzymes can cleave DNA and RNA between specific nucleases, creating fragments of DNA or RNA. Specific restriction endonucleases and exonucleases are well known to those skilled in the art. Examples of enzymes which cleave both DNA and RNA include, but are not limited to, snake-venom phosphodiesterase and spleen phosphodiesterase. Enzymes which cleave only DNA include, but are not limited to, deoxy-ribonuclease I and II. Ribonuclease I (pancreas) and T. (mold) cleave RNA.

When analyzing a biomolecule containing carbohydrate, it may be advantageous to add fucase, O- or N-glycanase, mannase, neuraminidase, galactosidase or glucosidase to the surface. These enzymes will generate carbohydrate fragments of specific molecular weight which can be determined in the mass spectrometer.

The complex attached to the sample presentation surface may also purify the biomolecule. For example, the complex may comprise a reactive molecule which invisibly binds common impurities such as detergents, lipids, endotoxins or proteases.

The present invention also provides a method for making the above-described derivatized mass spectrometry sample presentation apparatus. In this method it is essential that a complex which modifies biomolecules be bound to the surface of the sample presentation apparatus. In one embodiment, the entire complex is first synthesized or purified, and then reacted with the surface. In an alternate preferred embodiment, the complex is formed by first reacting the sample presentation surface with a tethering molecule, and then later reacting the tethered molecule with a reactive molecule.

Another embodiment of the present invention provides a method for analyzing a biomolecule. Specifically, the method involves: (1) providing a mass spectrometry sample presentation surface, (2) binding at least one complex on the surface wherein the complex includes at least one molecule which chemically modifies a biomolecule, (3) contacting the biomolecule with the surface, thereby chemically modifying the biomolecule (4) applying a MALDI matrix to the surface and (5) determining the molecular weight of the biomolecule in a mass spectrometer. The biomolecule may be contacted with the surface while in solution or in the vapor phase.

The contacting step is preferably performed above room temperature, most preferably up to 55° C., to speed the reaction rate. However, it should not be performed at a temperature high enough to cause degradation of the analyte or the complex. For certain complexes, it may be advantageous to perform the contacting step below room temperature, most preferably above −10° C. This contacting step is allowed to proceed for a sufficient time, typically 5–30 minutes. The actual reaction time will depend on the particular complex and biomolecule. When proteases are used to digest polypeptide biomolecule, the contacting step is preferably performed in a moist atmosphere. Such an atmosphere may be created for example, by providing a water reservoir and enclosing it along with the sample presentation surface and biomolecule in a closed system.

Next, a MALDI matrix is added to the reacted biomolecule. The MALDI matrix may be any material which solubilizes biomolecules, absorbs light energy at a frequency easily accessible by a laser, and is unreactive with respect to biomolecules. Suitable matrices include nicotinic acid, pyrozinoic acid, vanillic acid, succinic acid, caffeic acid, glycerol, urea or tris buffer (pH 7.3). Preferable matrices include α-cyano-4-hydroxycinnamic acid, ferulic acid, 2,5-dihydroxybenzoic acid, sinapic (or sinapinic) acid, 3,5-dimethoxy, 4-hydroxy-trans-cinnamic acid, other cinnamic acid derivatives, gentisic acid and combinations thereof.

A further embodiment of the present invention provides a mass spectrometer which incorporates the above-described sample presentation apparatus. The mass spectrometer according to the present invention further comprises a vacuum interlocking device for introducing the sample presentation apparatus into a volatilization chamber, an apparatus for volatilizing and ionizing the analyte, an optional electric field generator which is oriented to cause biomolecule ions to travel toward a detector, and electronics for determining the molecular weight to charge ratio for a particular ion based on its trajectory.

This mass spectrometer is compatible with all of the techniques normally used for volatilizing and ionizing analytes. Such techniques include, but are not limited to, electrospray ionization, Californium$^{252}$ plasma desorption, field desorption, fast atom bombardment, liquid secondary ion MS, laser desorption, and thermospray ionization. Preferably, the MALDI technique is used for volatilizing and analyzing biomolecules. The mechanical structures or equipment required in these techniques are well known to those skilled in the art.

The spectrometer usually contains an electric field generator which has electrically charged metal structures between the area in the spectrometer where the ions are generated and the detector. These structures must be designed such that they attract ions, but the ions can travel past them to reach the detector. Preferably, the structures are charged metal grids with apertures that allow some of the ions to pass through and drift toward the detector. The structures must be located between the ion generation area and the detector. They must also have a potential difference which acts to accelerate ions toward the detector.

Some mass spectrometers also use magnetic fields to deflect ions as they travel towards the detector. Such instruments determine the mass of an ion based on its deflection in the magnetic field. It is, however, preferable to use a time-of-fight mass spectrometer to determine the mass of biomolecules.

The electronics for determining the molecular weight to charge ratio of an ion based on its trajectory typically includes an ion impact detector, data-acquisition electronics, and data analysis electronics, such as a computer.

Many types of detectors are compatible with the present invention. Some specific examples of detectors include the Faraday cup, electron multipliers, electro-optical ion detectors and photographic emulsions.

Specific embodiments in accordance with the present invention will now be described in detail. These examples are intended to be illustrative, and the invention is not limited to the materials, methods or apparatus set forth in these embodiments.

EXAMPLE 1

Preparation of Sample Presentation Apparatus

Circles of gold (Au) foil (99.9%), available from Johnson Matthey, 2.5 mm diameter and 0.01 mm thick were punched out and placed in a polyethylene microcentrifuge tube. Care was taken to avoid any contamination of the gold foil circles. The gold foil was activated according to the method of Katz. See, Katz, E. Y., J. Electroanal. Chem., Vol. 291, p. 257 (1990). The circles were treated with a crosslinking, or tethering molecule, solution of Dithiobis [succinimidylpropionate] (DSP) available from Pierce dissolved in isopropanol to approximately 0.1M. The DSP/isopropanol solution was essentially saturated at this concentration. The circles were treated with the DSP/isopropanol solution for fifteen minutes, with occasional mixing using a vortex mixer. This tethering molecule solution was poured off, and the gold circles were rinsed repetitively with pure isopropanol, followed by three rinses with pure ethanol. The gold circles were vacuum dried and transferred to new microcentrifuge tubes prior to treatment with a reactant molecule or biomolecule.

EXAMPLE 2

Preparation of Sample Presentation Apparatus with Surface-Bound Trypsin

A mass spectrometry sample presentation apparatus was prepared by binding trypsin to the surface of the apparatus as follows. Trypsin type XIII: tosyl-L-phenylalanine chloromethyl ketone (TPCK) treated, from bovine pancreas available from Sigma, was dissolved in 20 nM phosphate buffer, pH 7.8 to a concentration of 1 mg/mL for use in preparation of the derivatized sample presentation apparatus. To attach the enzyme to the crosslinker or tethering molecule on the gold foil circles prepared in Example 1, the circles were incubated with a 1 mg/mL solution of enzyme in 20 mM phosphate buffer, pH 7.8 overnight in a refrigerator with occasional agitation. Following incubation, the gold foil circles were rinsed vigorously with the phosphate buffer, and subsequently with a 0.1% aqueous solution of Triton-X100, using a vortex mixer for both rinses. The gold foil circles were then vacuum dried and stored in polyethylene microcentrifuge tubes. Physical attachment of the gold foil circle surfaces to the stainless steel sample presentation apparatuses conventionally used for routine MALDI analysis was accomplished by application of a small amount of spray adhesive to the conventional sample presentation surface or probe tip, which was then pressed onto one of the gold foil circles. Prior to attachment, the conventional stainless steel (304) mass spectrometer sample presentation apparatuses were electropolished and thoroughly rinsed in deionized water followed by ultrasonic cleaning in methanol. Even pressure was maintained on the probe tip and gold foil while the adhesive was allowed to bond. The sample presentation apparatus with bound trypsin was then used for protein digestion as described hereinbelow. In practice, multiple tips were made and stored in polyethylene tubes at room temperature until needed.

EXAMPLE 3

Au/trypsin Sample Presentation Surface Contacted with Lysozyme

Digestions were performed with the Au/trypsin active surfaces prepared in Example 2 by the application of aliquots (either 4 μL or 400 nL) of 250 nM lysozyme hen egg solution (dissolved in 20 mM phosphate; 10 mM dithiothreitol (DTT); pH 8.1 buffer) directly to the sample presentation apparatus surfaces. The surfaces were allowed to stand in a humid enclosure maintained at 40° C. The solution volume on the surface was monitored, and additional aliquots of 1–2 μL of phosphate buffer were added if the volume of liquid appeared to be less than 2 μL. After 10 minutes the apparatus was removed from the humid environment, 2 μL of the MALDI matrix, a-cyano-4-hydroxycinnamic acid (prepared as a saturated solution in a solvent mixture of 2:1, 1.3% aqueous trifluoroacetic acid:acetonitrile (ACCA)), was applied and the surface was allowed to air dry.

COMPARATIVE EXAMPLE 4

Protein Digestion/Sample Preparation with Free Trypsin

A 1:1 mole ratio of trypsin to lysozyme was prepared by addition of 2 μL of 500 nM lysozyme with 2μL of 500 nM trypsin (both prepared in a 20 mM phosphate; 10 mM DTT; pH 8.1 buffer). The combined volume was placed in a 600 μL microcentrifuge tube and incubated at 40° C. for 10 minutes. The reaction was halted by the addition of 2 μL of the MALDI matrix ACCA and the total volume of the digest/matrix mixture was placed on an inert mass spectrometer sample presentation apparatus and allowed to air dry.

COMPARATIVE EXAMPLE 5

Agarose Immobilized Trypsin

A 1:1 volume ratio of lysozyme to agarose/trypsin was prepared by addition of 2 μL of 500 nM lysozyme with 2 μL of slurried agarose/trypsin (both prepared in a 20 mM phosphate; 10 mM DTT; pH 8.1 buffer). The slurried agarose contained approximately 1 μL of beaded reagent. The combined volume was placed in a 600 μL microcentrifuge tube and incubated at 40° C. for 10 minutes. The reaction was halted by the addition of 2 μL of ACCA matrix and the total volume (with beaded reagent) of the digest/matrix mixture was placed on an inert mass spectrometer conventional sample presentation apparatus or probe tip and allowed to air dry.

EXAMPLE 6

Time-of-Flight Mass Spectrometry

Mass spectrometry was performed using the sample presentation apparatus prepared in Example 3, Comparative Example 4, and Comparative Example 5 using a linear time-of-flight mass spectrometer. Desorption and ionization were accomplished using the third harmonic (355 nm) output of the Nd:YAG laser (Continuum Surelite I). The optical path of the laser contained a variable attenuator (Newport 935), a right-angle beam steering prism and a 250 mm focal length quartz lens placed approximately 300 mm from the sample target. Ions generated from the matrix/analyte sample were accelerated to a potential of 30 kV using a two-stage acceleration source (total distance=1.5 cm). An electrostatic particle guide was used to assist in ion transmission over the flight path. Detection was accomplished using a hybrid, microchannel-plate/discrete dynode, electron multiplier. Thresholds of ionization were determined empirically by increasing the intensity of the laser light at the sample surface while monitoring the ion signal real-time with a 50 Mhz oscilloscope (Tektronix TDS 310). Upon observation of stable ion signal, 50 laser shots were signal averaged using a 500 MS/s digital storage oscilloscope (Tektronix TDS 520A) and transferred to an IBM-compatible 486 computer. The data were analyzed using the PC compatible software LabCalc (Galactic Industries). All mass spectra were obtained in the positive-ion mode. External mass calibration was accomplished with the single and double-charged peaks of bovine insulin (MW=5,733.5 Da). Masses of digest fragments were calculated using the known hen egg lysozyme amino acid sequence and the peptide data manipulation routine PROCOMP. This program is publicly available from Dr. Philip C. Andrews, University of Michigan Medical Center, Ann Arbor, Mich. 48104.

Figure 1A:
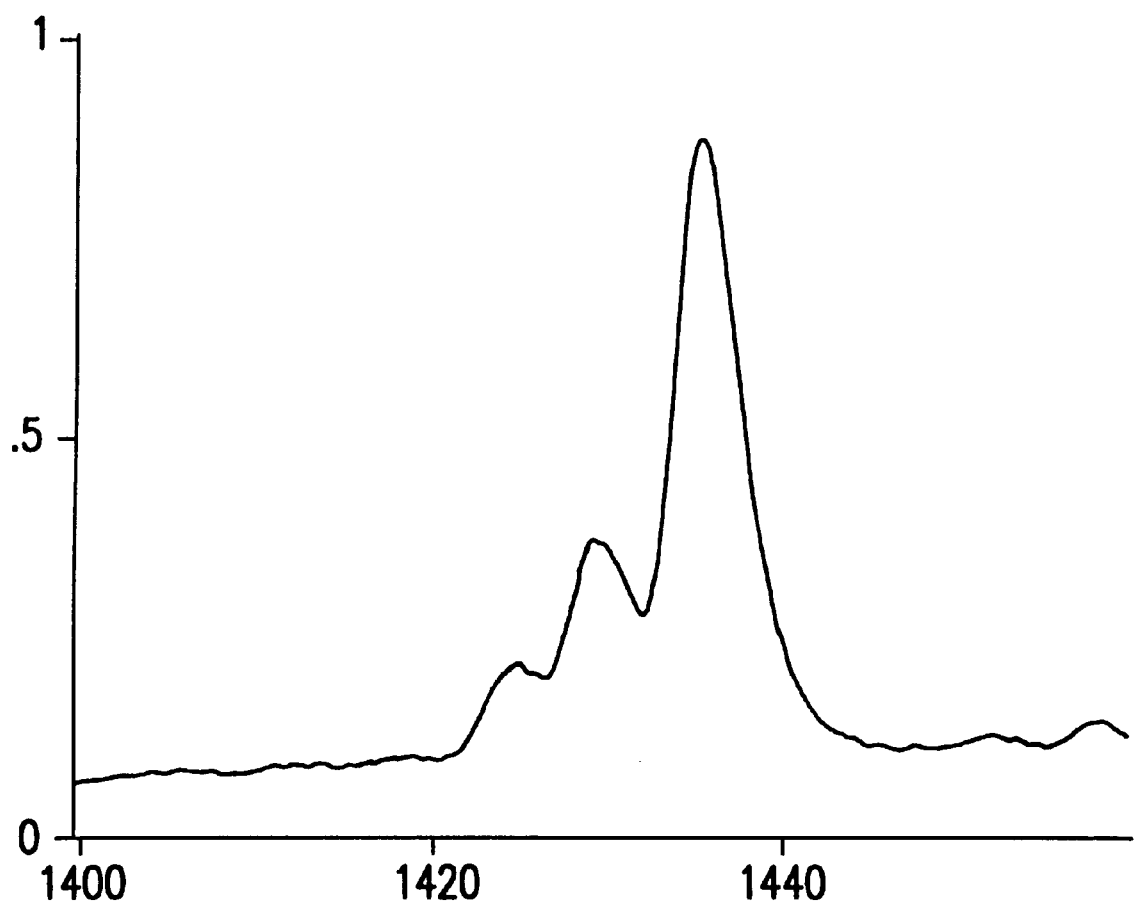
FIG. 1A is a MALDI mass spectrum of 10 picomoles of chicken egg lysozyme digested for 10 minutes with surface-bound trypsin.

Prior to enzymatic cleavage, the integrity of the lysozyme samples was verified through MALDI analyses using sample presentation apparatus without any bound complex. No signals other than those due to the lysozyme ions, singly-and multiply-charged signals, were observed during these analyses. FIG. 1 shows the results of a 10 minute digestion (40° C.) of 10 picomoles of lysozyme using the sample presentation apparatus with trypsin bound to the gold surface as described in Example 3. No signals were observed over m/z=6,000, which indicates high trypsin activity. Ion signals are observed for 33 out of 67 possible digest products (in the mass range up to 6,000 Da). Signals below m/z=1,000 Da were generally not considered because of possible interferences from the matrix. Signal intensity and quality was such to allow laser desorption conditions capable of resolving tryptic fragments at m/z=1,424.8, 1,429.6 and 1,435.5 Da (FIG. 1A). FIG. 2 shows the correlation between the calculated masses of the enzymatically cleaved fragments and those observed in the mass spectrum.

Figure 3:
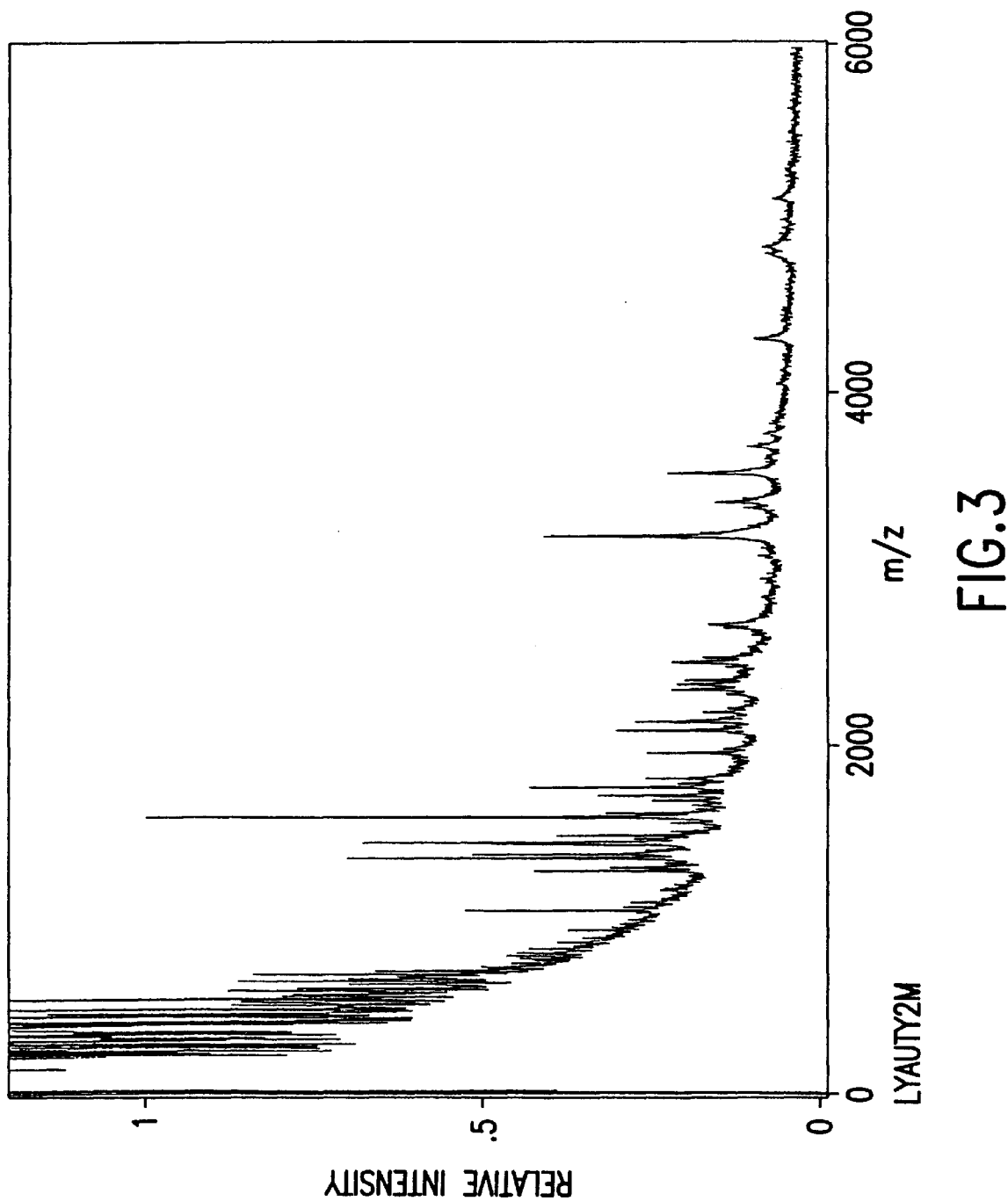
FIG. 3 is a MALDI mass spectrum of 1 picomole of chicken egg lysozyme digested for 10 minutes with surface-bound trypsin.
Figure 3A:
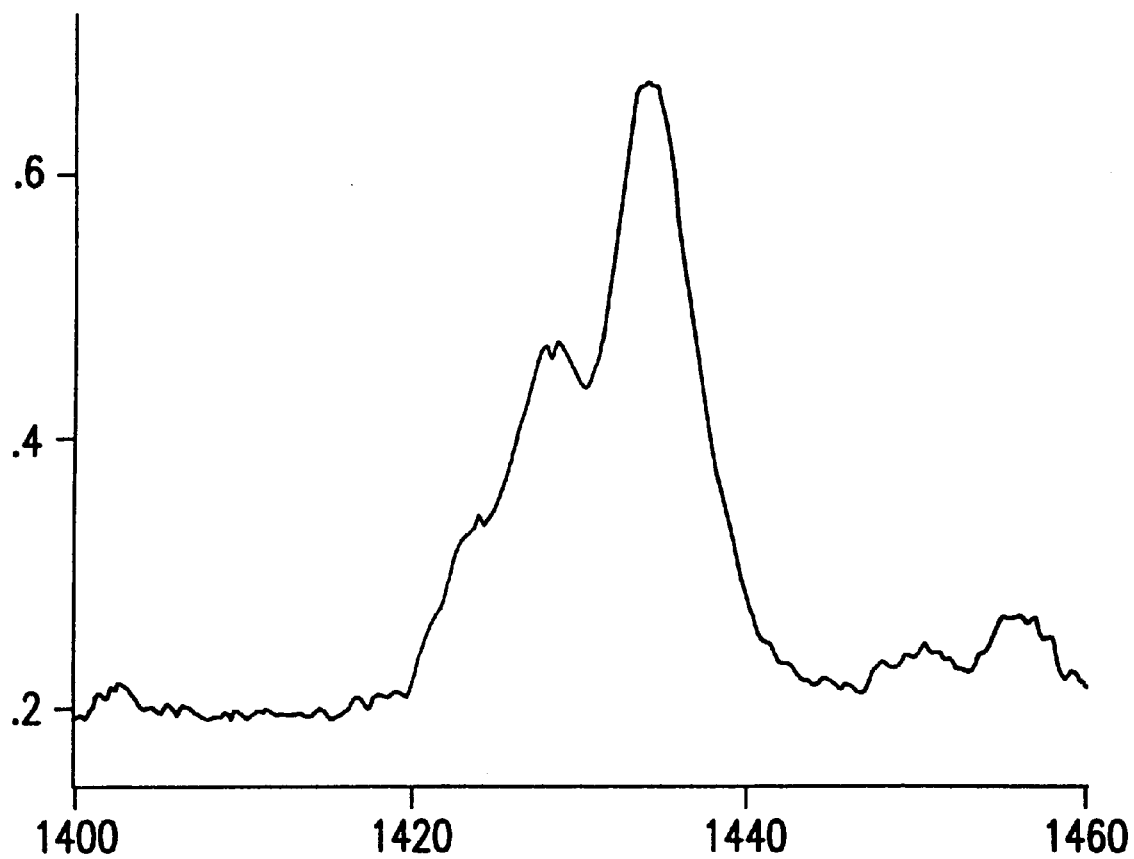
FIG. 3A is a MALDI mass spectrum of 1 picomole of chicken egg lysozyme digested for 10 minutes with surface-bound trypsin.

FIGS. 3 and 3A show the mass spectrum obtained from using the same procedure performed with only 1 pmol of lysozyme applied to the surface. Virtually the same fragmentation pattern is observed, with an expected sacrifice in the signal-to-noise ratio of the data.

Figure 4:
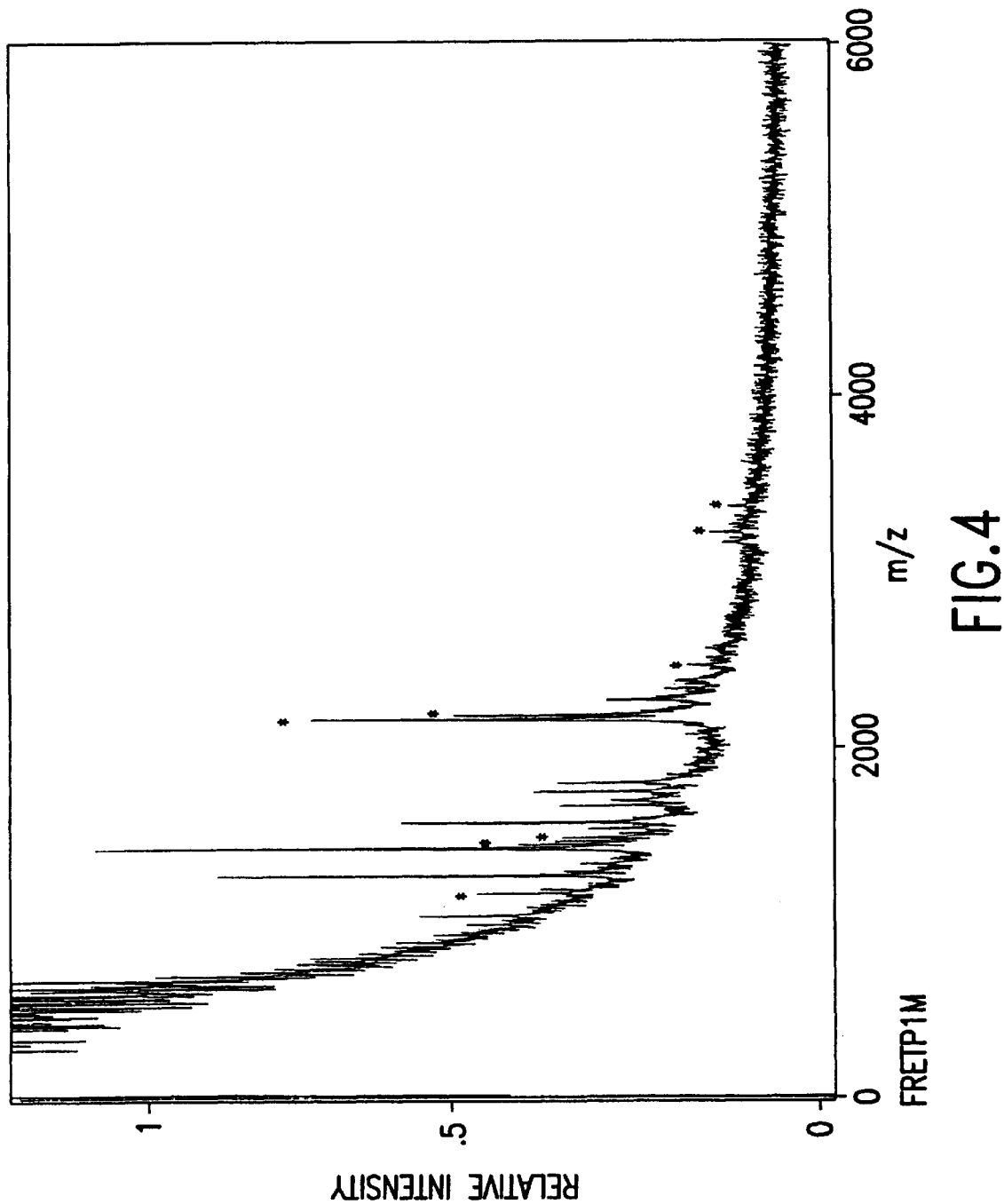
FIG. 4 is a MALDI mass spectrum of 1 picomole of chicken egg lysozyme digested for 10 minutes with an equimolar amount of unbound trypsin.

For comparison, 1 pmol of lysozyme was digested using either an equal mole ratio of free trypsin or an equal volume of agarose immobilized trypsin as described in Comparative Examples 4 and 5. Results of the digestion using free trypsin are shown in FIG. 4. Many of the low mass signals compliant with trypsin-generated fragments are observed which are shown in FIG. 6. Strong signals at m/z 1177, 1459, 1498, 2166, 2191, and 2275, however, are attributed to autolysis products of the trypsin since these fragments are also observed during the MALDI mass analysis of trypsin as shown in FIG. 6.

Additionally, trypsin whole molecule signals (singly- and multiply- charged signals) also appear in the spectrum. The autolysis and parent signals contaminate the data because these fragments are incorporated in the matrix. The trypsin used in digestion is not bound to the surface, and therefore, there is nothing to prevent the trypsin molecular ion and autolysis products from incorporating into the matrix crystals. In addition, a decrease in the signal-to-noise ratio is also observed, relative to FIGS. 3 and 3A, and is attributed to loss of sample in transfer and handling.

Figure 5:
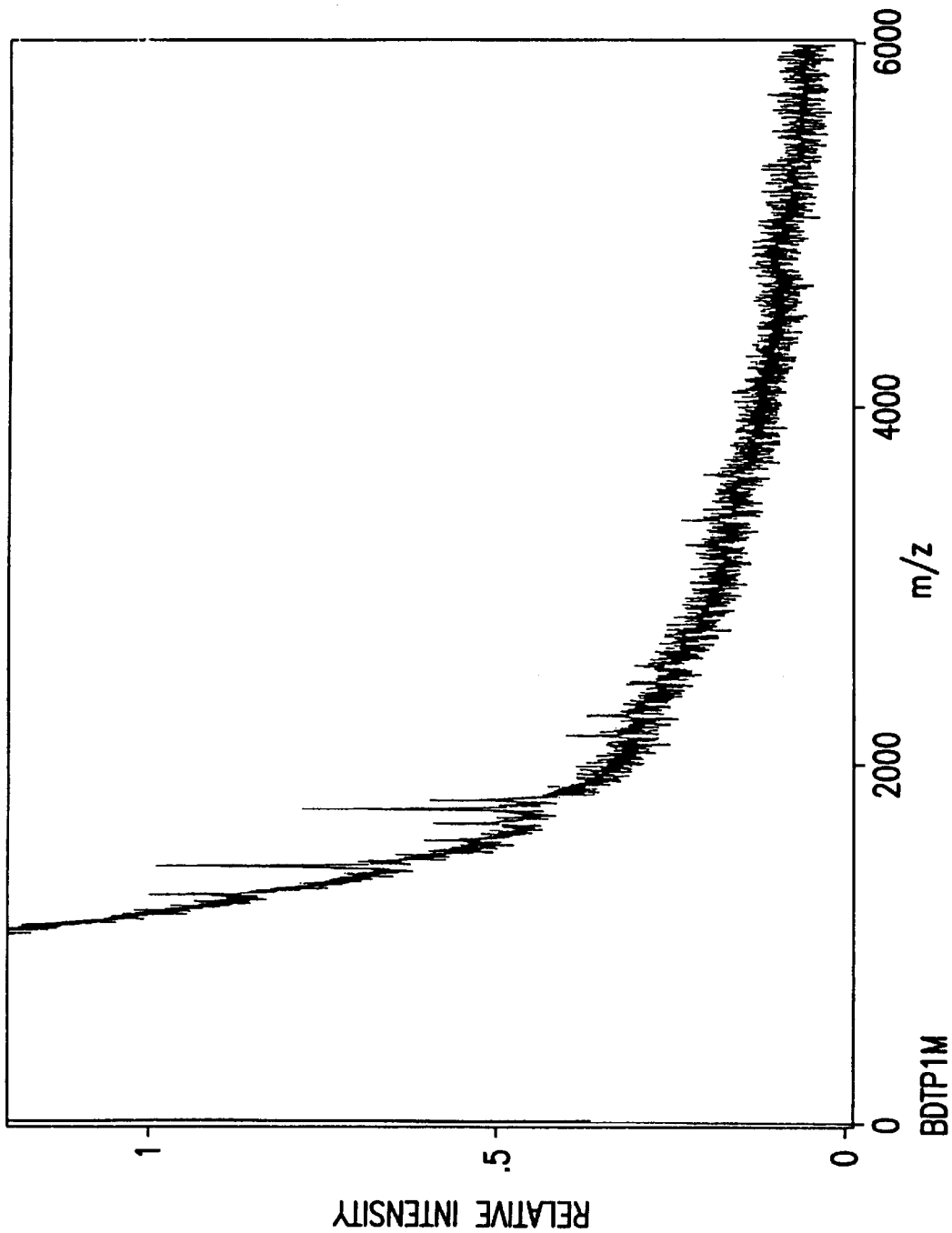
FIG. 5 is a MALDI mass spectrum of 2 $\mu$l of a 500 $\mu$M solution of chicken egg lysozyme digested with an equal volume of slurried agarose immobilized trypsin.

Agarose-immobilized trypsin was used in order to attempt to reduce the background contribution due to the trypsin autolysis products. The results obtained from the 10 minute, 40° C. digestion of 1 pmole of lysozyme using approximately 1 μL of beaded agarose as described in Comparative Example 5 are shown in FIG. 5. Signals are observed for nine lysozyme digest fragments, and only two autolysis product peaks at m/z 2164 and 3371 are found. In contrast to both the derivatized sample presentation apparatus and the free trypsin digestions, few peaks corresponding to digest fragments are observed. However, a marked decrease in the overall signal intensity is observed. Since the agarose is a porous medium, it is believed that digest fragments are lost through a combination of incorporation into the media, slow digestion due to poor localization of analyte around the immobilized enzyme, and inefficient elution using a small volume of matrix.

Comparing the spectrum obtained using the Au/trypsin derivatized sample presentation apparatus with those of the immobilized and free trypsin digests, it is clear that digests performed using the derivatized sample presentation apparatuses are noticeably free of background signals due to enzyme autolysis products and maintain a high level of activity. It is estimated from the digest pattern which indicates the degree of total digestion that the activity of the derivatized surfaces in accordance with the invention falls somewhere between that of the agarose-immobilized and free trypsin (approximately 0.05 and 0.15 TAME units, respectively). This level of derivatized surface activity has been found to remain reasonably consistent from batch to batch if similar preparation conditions, e.g., incubation time, temperature, and buffer, are used. However, activity has been found to be seriously impaired if the surfaces are inadvertently touched resulting in deposition of oils, or contaminated with adhesive during the fixing of the Au/trypsin foil to the conventional sample presentation apparatus. Care must be taken in the final steps of surface preparation. Alternatively, the risk of contamination has been completely eliminated by sputter-coating the surfaces with gold and coupling trypsin directly to this gold coating. Trypsin activity using this method was found to be approximately equal to that of the gold foil method.

EXAMPLE 7

Au/trypsin Sample Presentation Surface Contacted with α-cobratoxin

α-cobratoxin was analyzed using an immobilized trypsin sample presentation apparatus as described in Example 2.

First, the unfragmented α-cobratoxin was analyzed using the MALDI method. Signals were obtained which correspond the singly and doubly charged ions of the intact peptide. As can be seen from FIG. 7 and FIG. 8, singly and doubly charged ions corresponding to residue 1–71 are observed at 7,823 and 3,912 Da, respectfully. Signals less than m/z approximately 1,000 Da are due to the ACCA matrix.

Figure 7:
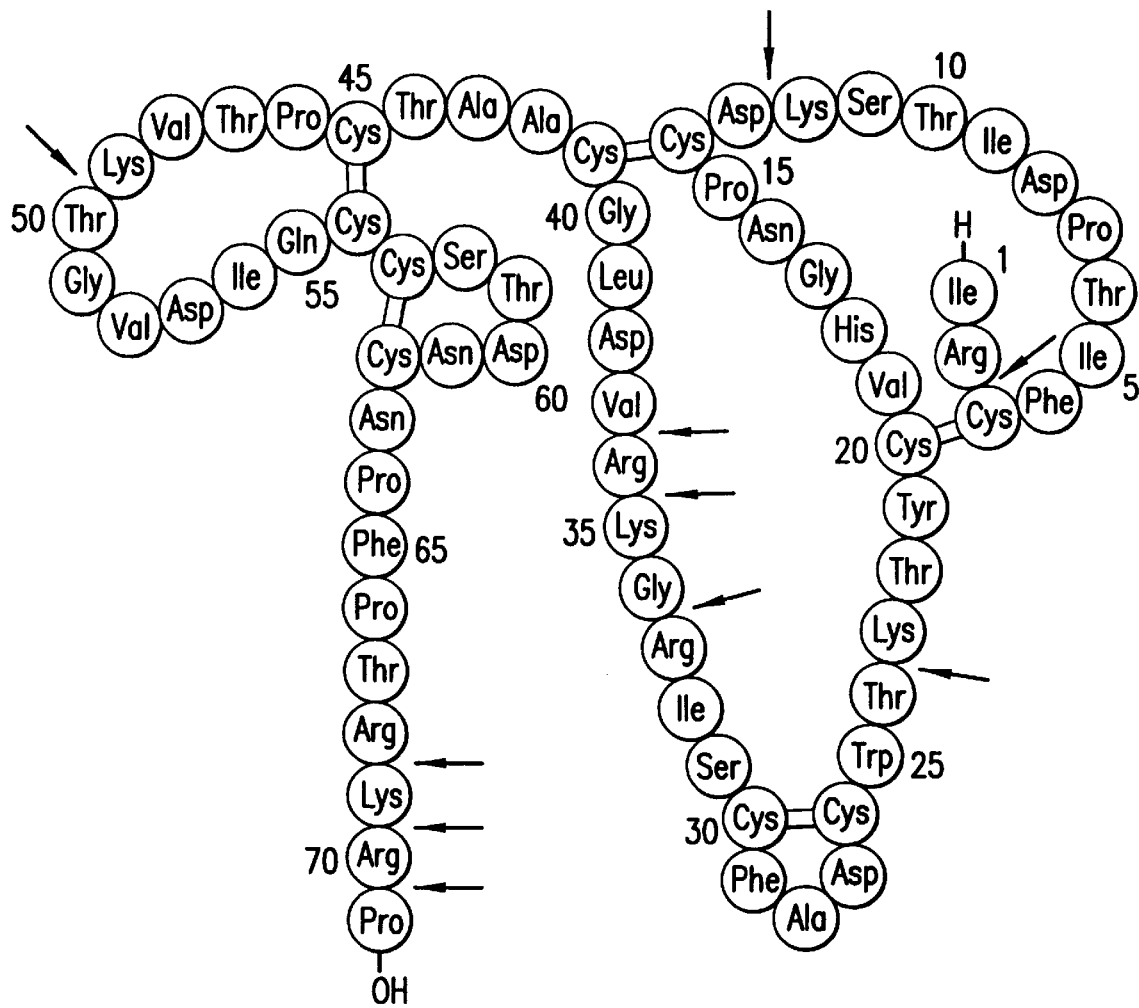
FIG. 7 is a schematic illustration of the amino acid sequence of α-cobratoxin.
Figure 9:
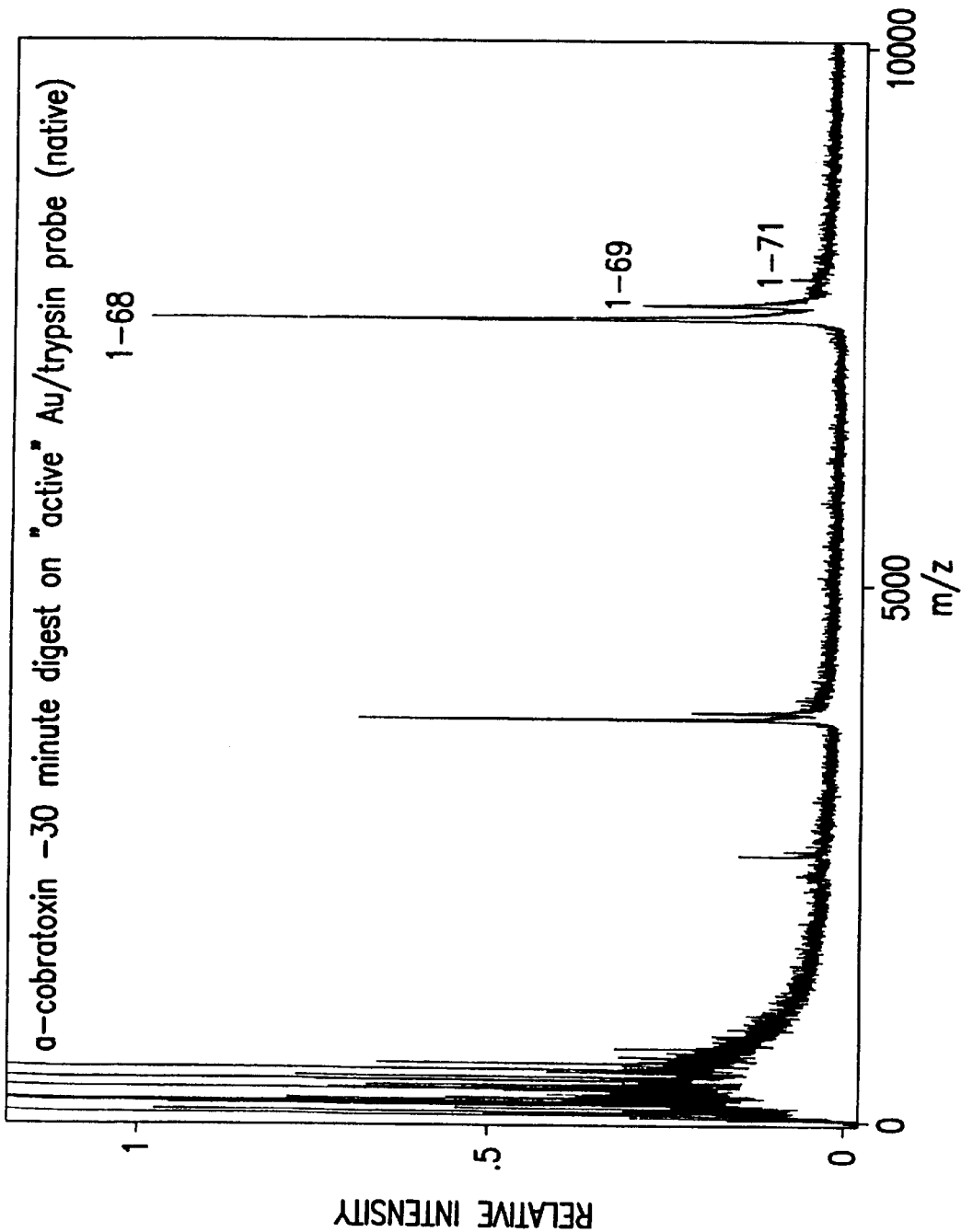
FIG. 9 is a MALDI mass spectrum of approximately 10 picomoles of α-cobratoxin digested for 30 minutes with surface-bound trypsin sample presentation apparatus.
Figure 12:
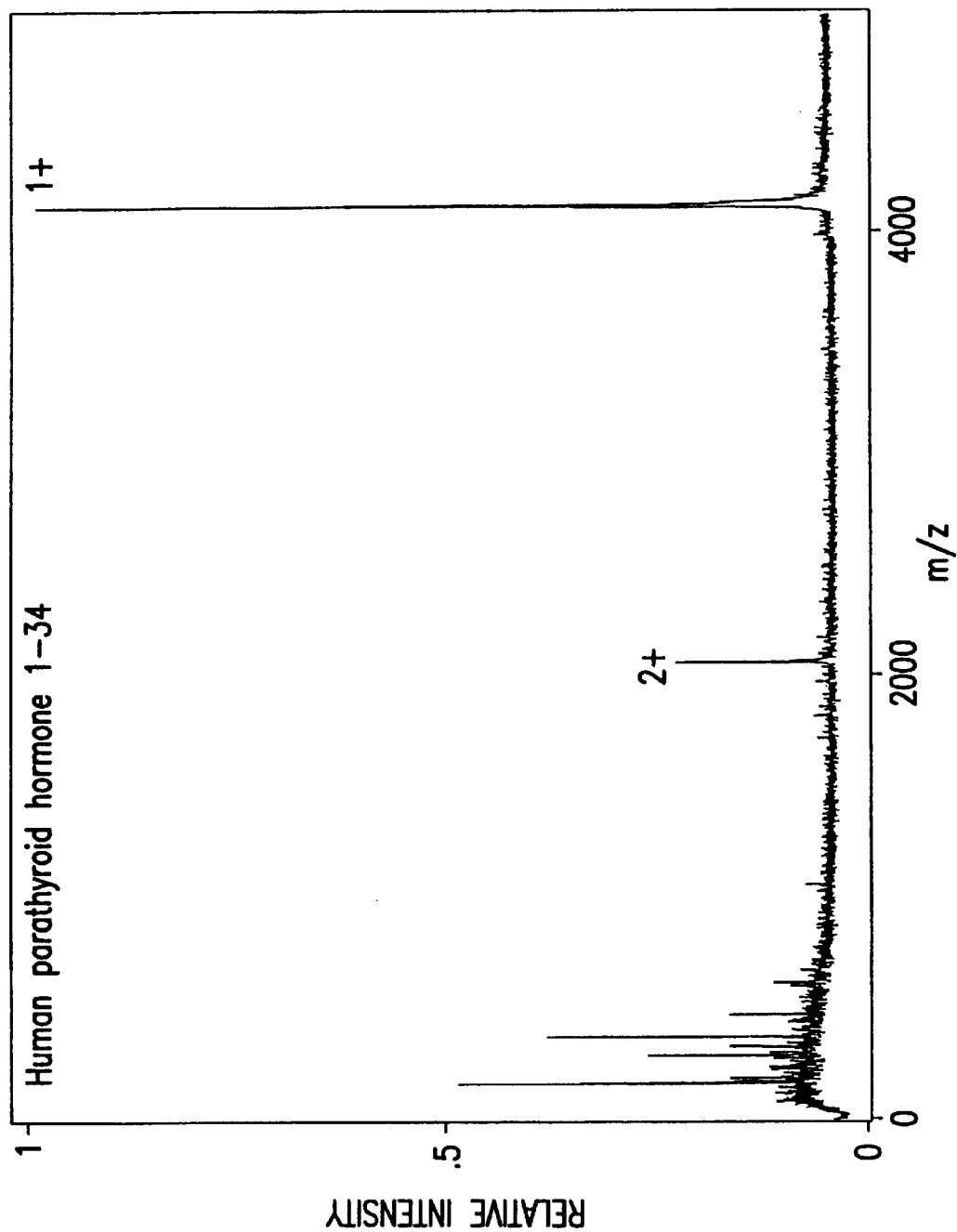
FIG. 12 is a positive ion MALDI mass spectrum of undigested human parathyroid hormone 1–34 (hPTH).
Figure 13:
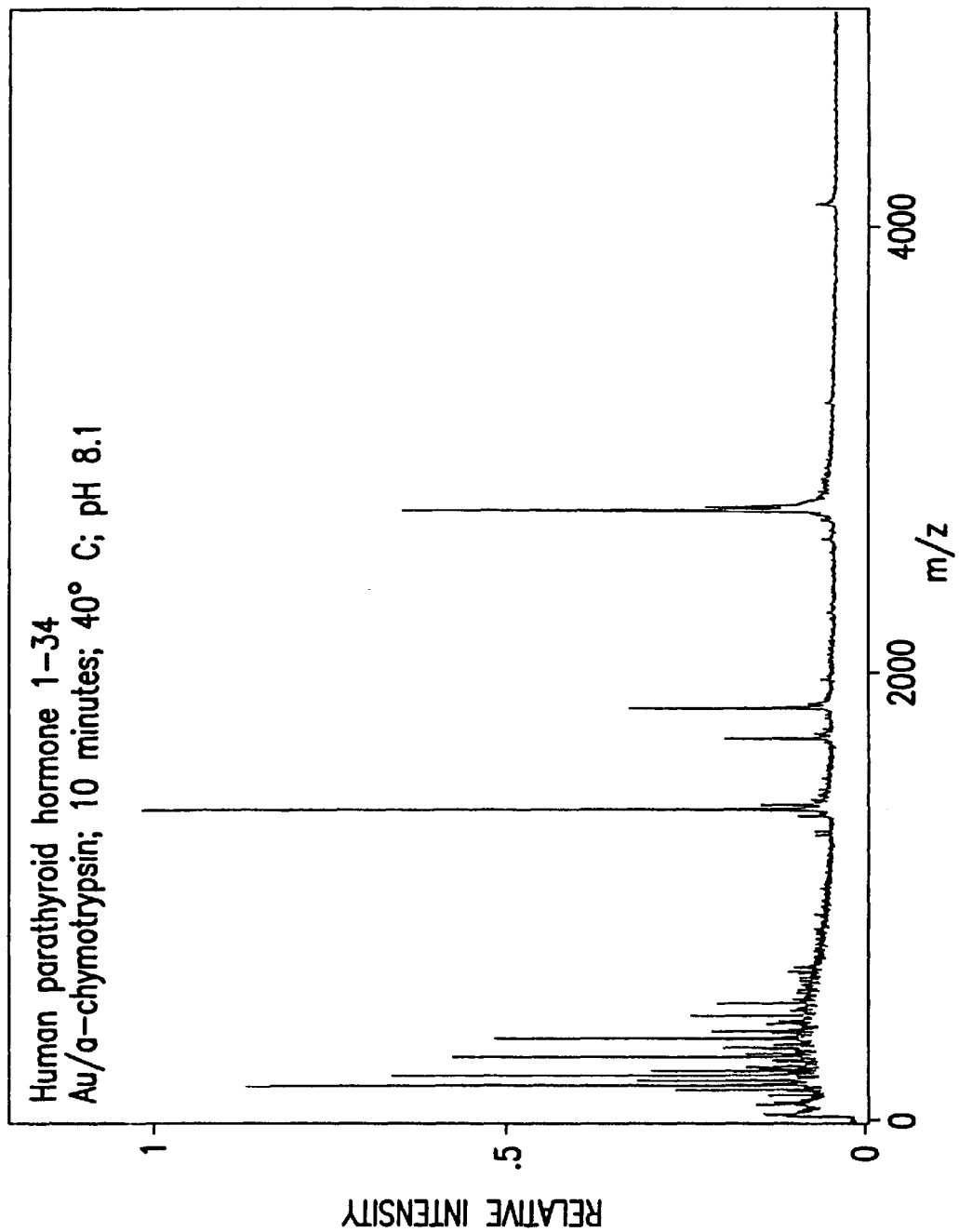
FIG. 13 is a MALDI mass spectrum of hPTH digested for 10 minutes on a surface-bound α-chymotrypsin mass sample presentation apparatus.

Next 10 picomoles of α-cobratoxin were digested for 30 minutes with a trypsin surface prepared according to Example 2. The α-cobratoxin was applied to the surface in a 3 μL volume of 10 mM phosphate buffer (pH 7.8). The reaction was allowed to proceed in a highly humid environment, at room temperature, for 30 minutes before being stopped by the addition of an equal volume of ACCA matrix. The mixture was allowed to dry before being inserted into the mass spectrometer. The resulting mass spectrum, shown in FIG. 9, shows singly and doubly charged ion signals for peptides with molecular weights of 7,445, 7,575 and 7,823 Da. These weights correspond to peptide sequences 1–68, 1–69 and 1–71, respectively, as shown in FIG. 7. These are the primary fragments expected from the tryptic treatment of the non-reduced peptide. Five other cleavage sites are possible, each producing different molecular weight fragments. However, these sites are stearically hindered and not available to trypsin. Therefore, these five other possible peaks were not observed. α-cobratoxin was further analyzed by repeating the above-described 10 picomole α-cobratoxin digestion by surface-bound trypsin in the presence of a reducing agent (10 pmol α-cobratoxin in 3 μL–10 mM phosphate; 10 mM DTT). As can be seen from FIG. 7, the reducing agent broke the disulfide bonds, thus enabling the generation of more fragments. The resulting spectrum shown in FIGS. 10 and 11 shows a set of peptide fragments indicative of reduced cobratoxin.

EXAMPLE 8

Figure 14:
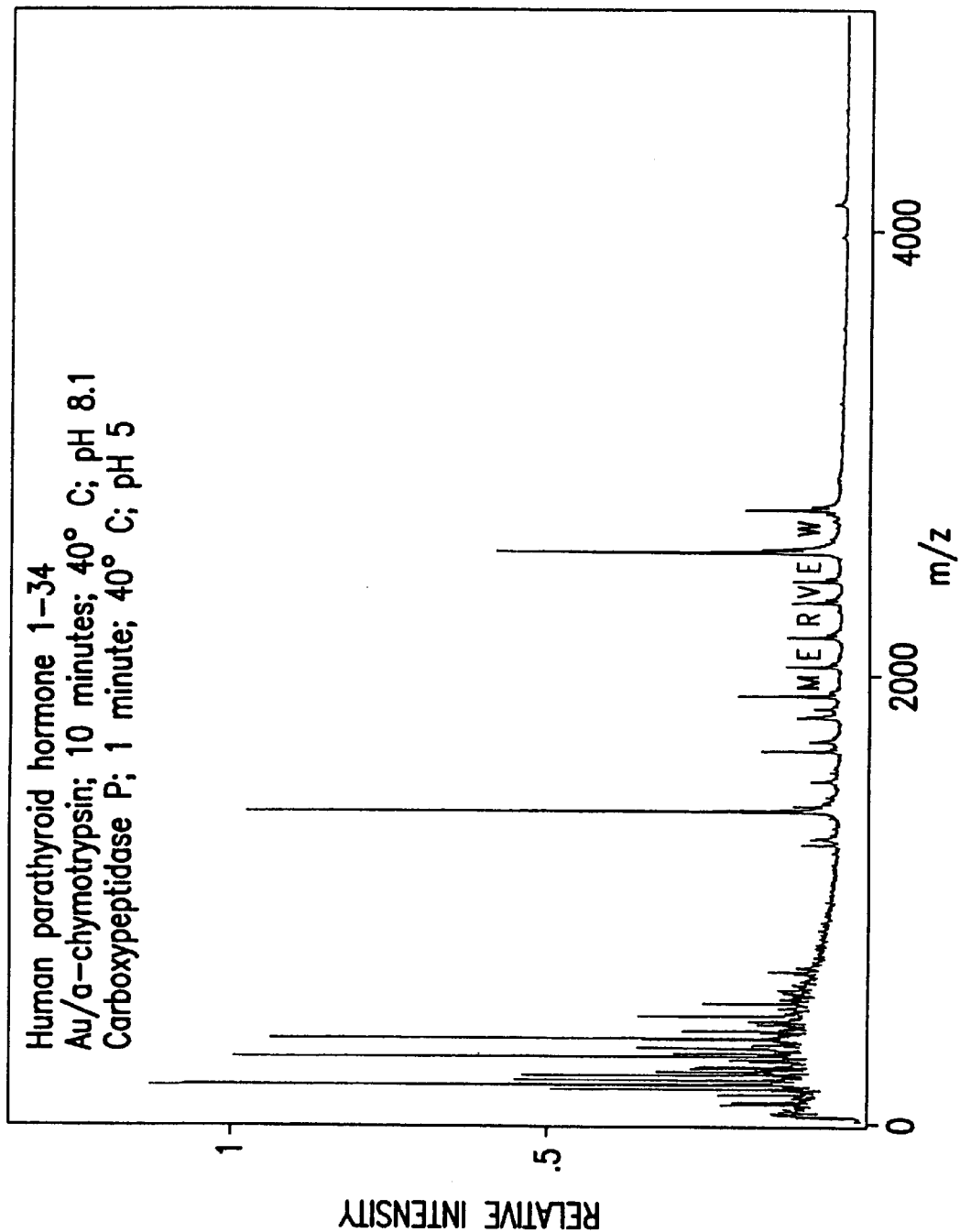
FIG. 14 is a MALDI mass spectrum of hPTH digested for 10 minutes on a surface-bound α-chymotrypsin sample presentation apparatus followed by pH adjustment to approximately 5 and addition of carboxypeptidase P (cpp). The inset illustrates the region of interest for final residue determination.
Figure 14A:
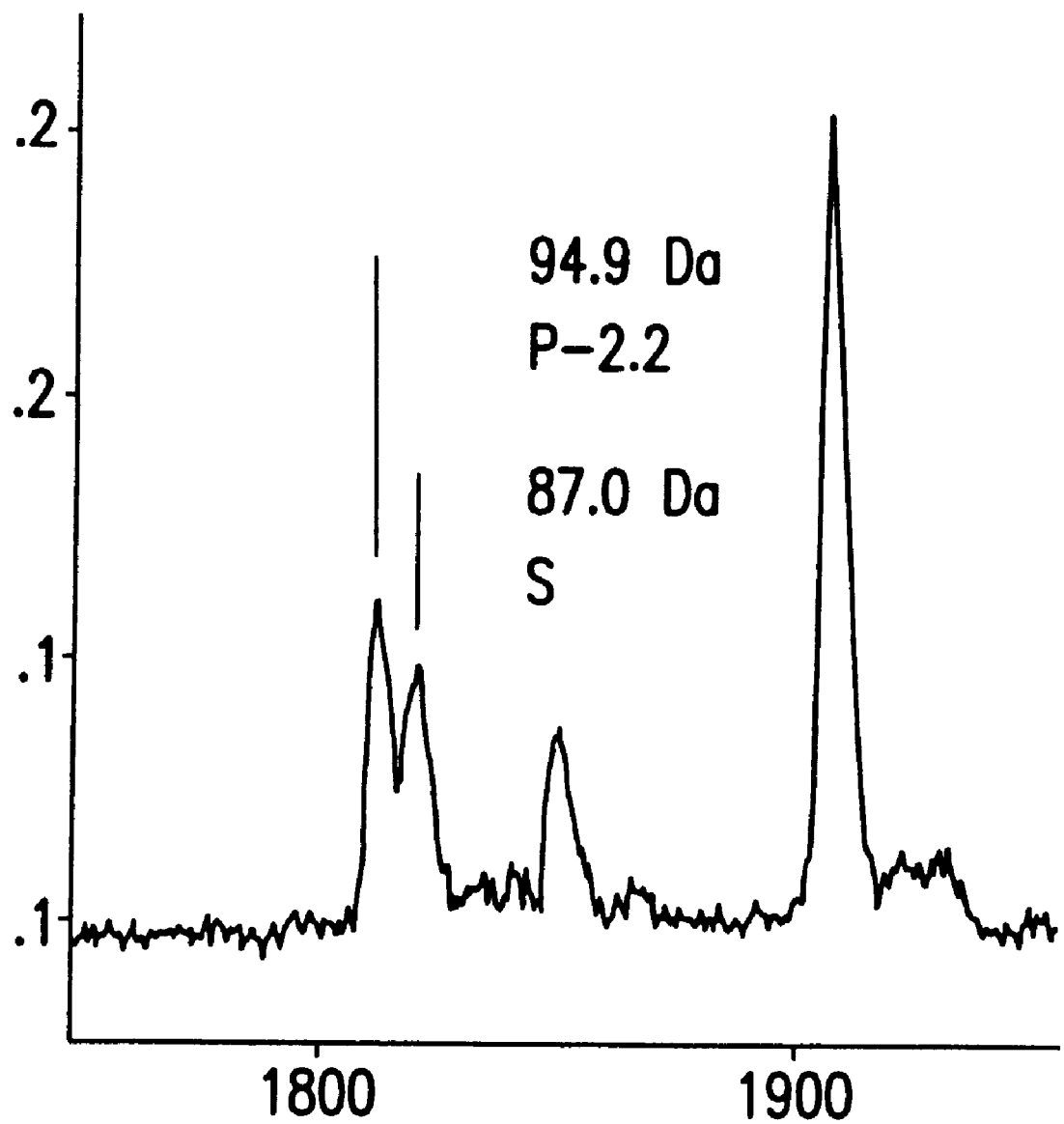

Preparation of Sample Presentation Apparatus with Surface-Bound α-Chymotrypsin A mass spectrometry sample presentation apparatus was prepared by binding α-chymotrypsin to the surface of the apparatus as follows. α-chymotrypsin or TPCK-treated α-chymotrypsin was dissolved in 20 mM phosphate buffer, pH 7.8 to a concentration of 1 mg/mL for use in preparation of a derivatized sample presentation apparatus as described in Example 2.

EXAMPLE 9

Sequence Determination For Design of Nucleic Acid Probes And Gene Identification The combination of surface-immobilized and free-peptidases were used to generate heterogeneous fragment mixtures from an original peptide as follows.

Enzymatically active trypsin and α-chymotrypsin mass spectrometry sample presentation surfaces were prepared as described in Examples 2 and 8.

The synthetic peptide human parathyroid hormone 1–34 (hPTH) was chosen as a test peptide for analyses. The sequence of the peptide is:

```
         10         20         30
SVSEIQLMHN LGKHLNSMER VEWLRKKLQD VHNF
```

Digestions were performed in the following manner. Three microliter aliquots of a 0.01 mg/mL solution of hPTH (in a buffer of 20 mM $NaHPO_4$, pH 8.1) were applied to derivatized mass spectrometer sample presentation apparatus prepared in accordance with Example 2 or Example 8. The digestion was carried out in a high humidity environment at a temperature of between 40 and 50° C. The digestions were allowed to run for 5 to 10 minutes before 0.5–1.0 μL aliquots of the reaction mixtures were removed from the surfaces. These aliquots were MALDI analyzed for endopeptidase mapping. The pH was reduced to approximately 5 with the addition of an aliquot of 20 nM $NH_4COOCH_3$, the volume of which was equal to that of the remaining reaction mixture. 500 nL aliquots of 0.001 mg/mL carboxypeptidase P (CPP), in the acetate buffer, were then added to the reaction mixtures. Protein ladder digestions were allowed to run for between 1 to 3 minutes before the surfaces were removed from the heated high humidity environment and the reactions halted through the addition of an equal volume of MALDI matrix. The matrix/reaction mixture was allowed to air-dry and the enzymatically-active surfaces inserted directly into the mass spectrometer.

FIG. 12 is an ACCA-MALDI mass spectrum of 2.5 picomoles of the hPTH, the starting point of reference for the following enzymatic analyses. A strong singly-protonated signal is observed at a mass-to-charge ratio (m/z) of 4,119.0 Da, a doubly- charged at m/z=2,019.7 Da, and little else other than matrix ion signals at m/z<500 Da.

The hPTH was further analyzed after a 10 minute digestion on an Au/α-chymotrypsin surface maintained at 40° C., pH 8.1. The results of this digestion are shown in FIG. 13. Four major signals at 1,398.5, 1,706.2, 1850.0 and 2,738.7 Da are observed as shown in FIG. 13.

Before adding the MALDI matrix to obtain the mass spectrum shown in FIG. 13, a portion of the digested peptide was transferred to a second conventional sample presentation apparatus surface. The portion of the digested peptide on the second conventional sample presentation surface was adjusted to a pH of approximately 5 and further exposed to cpp. FIGS. 14 and 14A show the MALDI mass spectrum obtained from this second sample. A series of ion signals due to cpp digestion is observed in the m/z range of 1,800–2,800 Da, presumably stemming from the Au/a-chymotrypsin digest signal at m/z=2,738.7. The first residue is a preferred cleavage site for α-chymotrypsin. FIG. 15 summarizes the masses of the signals observed in FIGS. 14 and 14A show the differences in mass between adjacent signals and the residues determined from the differences. The partial sequence (read as shown in FIG. 15 from N to C-terminal is determined by sequential mass difference to give (pep)-MERVEW-COOH.

Figure 16:
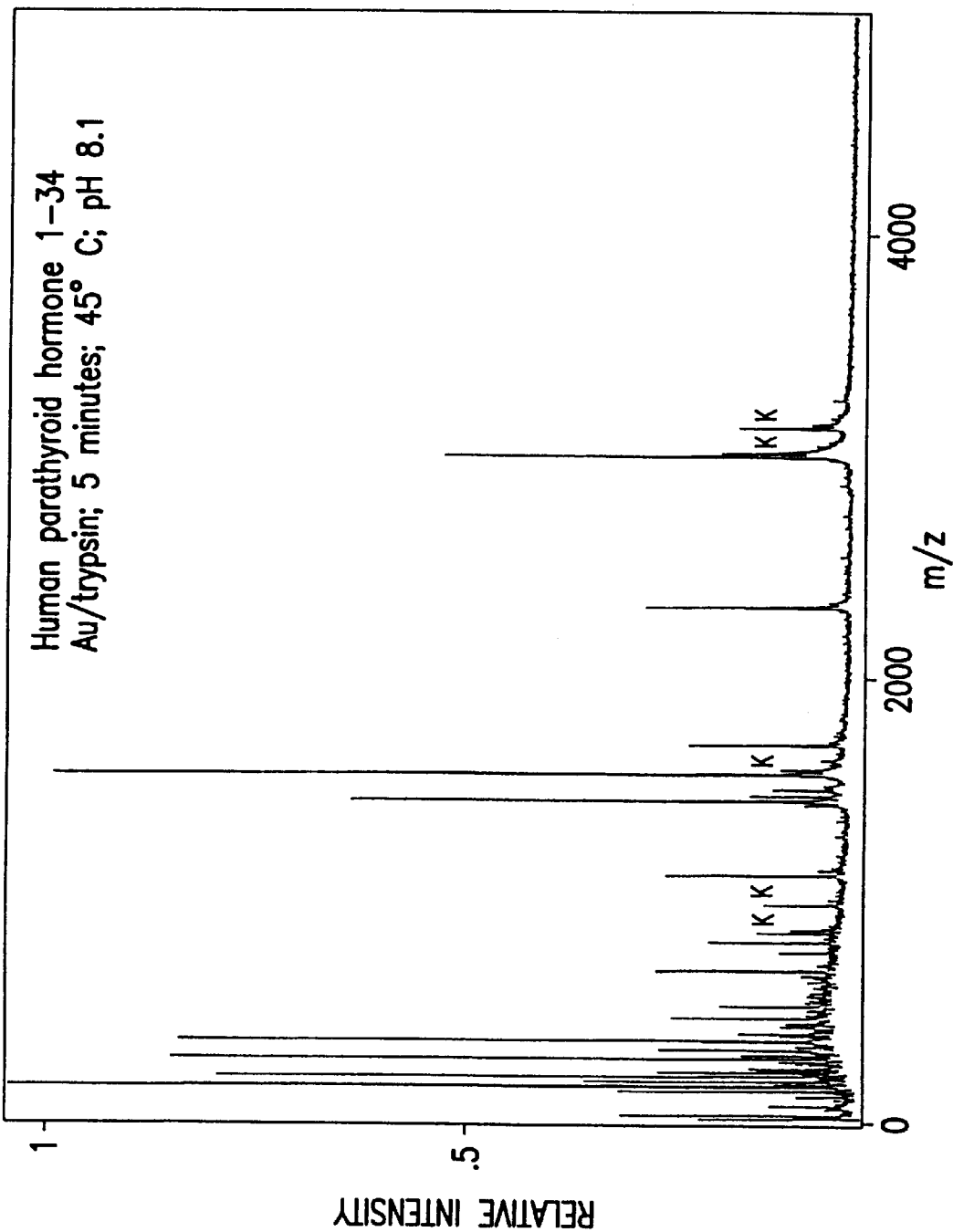
FIG. 16 is a MALDI mass spectrum of hPTH digested for 5 minutes on a surface-bound trypsin sample presentation apparatus maintained at 45° C., pH 8.1.
Figure 18:
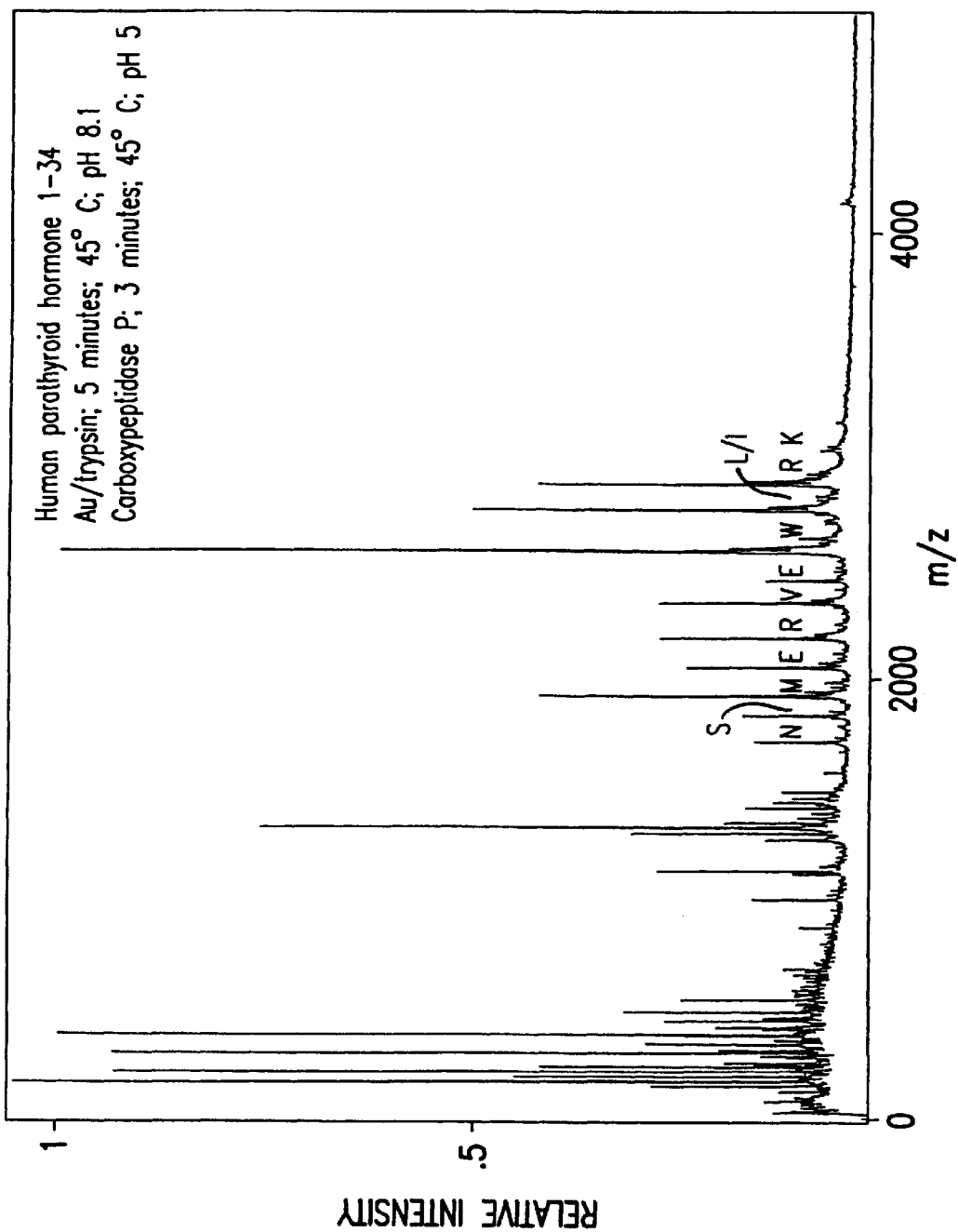
FIG. 18 is a summary of the partial peptide sequence generated by analyzing the mass spectrometry data from trypsin and trypsin/cpp fragments.

A second similar analysis of the hPTH was performed using an Au/trypsin sample presentation surface followed by cpp digestion. FIG. 16 shows the results of the Au/trypsin digestion after 5 minutes at a temperature of 45° C. (pH 8.1). FIG. 18 summarizes the masses observed for the digestion. The trypsin digestion shown in FIG. 16 resulted in the production of several starting fragments, and indicated the presence of the short sequence (Arg/Lys)-Lys-Lys.

Figure 17:
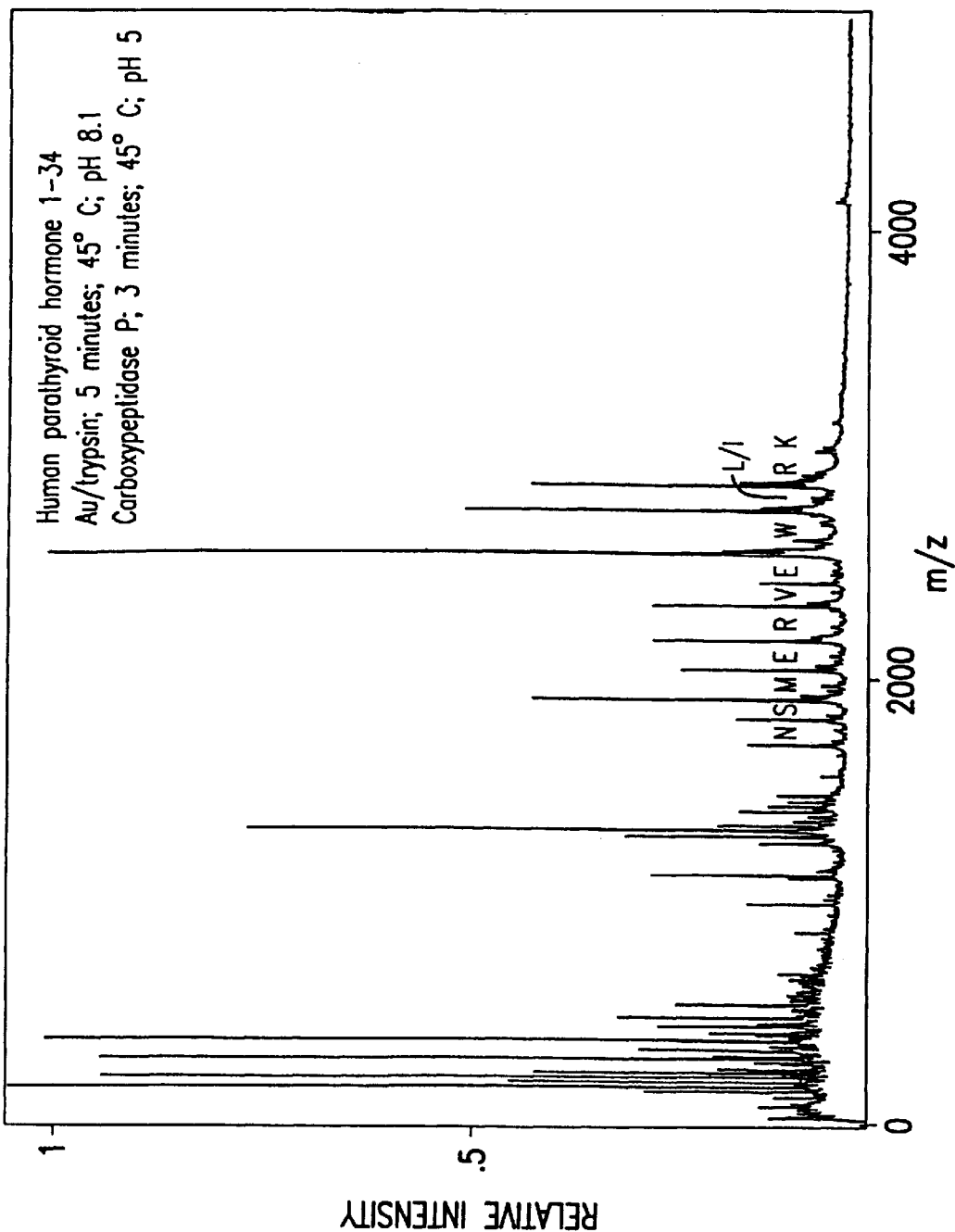
FIG. 17 is a protein ladder sequence generated by addition of cpp to the digested sample of FIG. 16.

Before adding the MALDI matrix to obtain the mass spectrum shown in FIG. 16, a portion of the digested peptide was transferred to a second, conventional sample presentation apparatus surface. The cpp was then added to this second portion. After pH adjustment to approximately 5, the ladder digestion was allowed to proceed for 3 minutes before being terminated by the addition of ACCA to the sample presentation surface. FIG. 17 shows the resulting sequence ladder. From the observed mass differences summarized in FIG. 18 the sequence was determined to be (pep)-NSMERVEW(L/I)RK-COOH. The first residue cleaved by cpp is that of Arg. Arg is a preferred cleavage site for trypsin. This is obviously an extension of the partial sequence determined using Au/α-chymotrypsin/cpp.

The large scale sequence, (Arg/Lys)-Lys-Lys, overlaps with the ladder sequence at correct mass. This allows both spectra to be combined for sequence extension by an additional Lys. The first residue observed in the Au/α-chymotrypsin/cpp series, from the C-terminal end, was determined to be tryptophan. This is expected because tryptophan is one of the preferred sites of α-chymotrypsin cleavage.

There are two ion signals to chose from in the region of the last cleavage of the Au/α-chymotrypsin/cpp digestion as can be seen from FIG. 15, inset, leading to the possibility of an ambiguity. The two mass differences represent the possibility of either a serine or a proline as the final residue. On the basis of the mass assignment error observed in the entire series (average approximately 0.15 Da), the final determination of serine, with −0.1 Da error was made over that of proline (with −2.2 Da error). The resulting sequence was determined to be (pep)-SMERVEW-COOH.

A nominal mass difference of 128 Da was observed at several points in the spectrum resulting from the initial trypsin cleavage in the Au/trypsin/cpp analysis. Considering that trypsin will cleave only at lysine or arginine, the 128 Da mass difference is highly likely to result from a lysine C-terminal to either another lysine or an arginine. Likewise, two adjacent mass differences of 128 Da, as observed in the 3,000 to 3,300 Da region, indicates the presence of Lys-Lys in the sequence, with the third residue being either another lysine or an arginine. This information, in combination with recognizing overlaps in the endo- and exopeptidase spectra, allows the two spectra to be used in combination to extend the sequence determination. FIG. 19 illustrates a ladder sequence extended by an additional lysine determined from the (Arg/Lys)-Lys-Lys observed in the trypsin spectrum overlapping with the Arg-Lys of the ladder sequence. The 128 Da mass differences observed in this manner can be unambiguously assigned to Lys as opposed to Gln which has the same molecular weight. The result is that 12 residues of the sequence were determined to be (pep)-NSMERVEW(L/I)RKK-COOH.

In gathering this data, four 50 to 100 laser-shot mass spectra, with quality and signal-to-noise great enough to determine relative molecular masses within approximately 0.2 Da, were generated using a total of approximately 15 picomoles of sample. Typical of the MALDI process, the sample preparations were capable of thousands of single laser-shot mass spectra of equal quality. As no special efforts were taken to minimize the amount of sample applied to the sample presentation surface apparatus, and the surface area of the apparatus was quite large, it may be possible to reduce the analyte sample amount, without sacrificing quality, by simply downscaling the whole process by reduction of surface area and application of less analyte sample.

It was important to maintain the derivatized sample presentation surfaces at elevated temperatures in order to perform these digestions rapidly. The temperatures used for both the endo- and exopeptidase digestions, performed at elevated temperatures of up to approximately 55° C., are somewhat above that typically used in proteolytic digestions, namely, 37° C. This, combined with the high relative activity of the enzymatically-active sample presentation surfaces, is believed to be responsible for the rapid analysis times. Although not guaranteed in every case, the 15 minute analysis time demonstrated in hPTH example represents a rate of analysis of just under one residue per minute.

After a peptide sequence is determined by the above-described process, the rules of degeneracy can be used to identify many nucleic acid sequences which code for the peptide sequence. See, e.g., *Biochemistry*, Stryer, pp. 91–115 (1988). Since many different nucleic acid sequences code for a single peptide, several nucleic acid sequences can be generated from the peptide sequences. The nucleic acid sequences can be used to search a database of nucleic acid sequences, e.g., Genbank, to identify genes which code for a particular polypeptide.

EXAMPLE 10

Preparation of Sample Presentation Apparatus with Surface-Bound Pepsin

A mass spectrometry sample presentation apparatus was prepared by binding pepsin to the surface of the apparatus as follows. Gold foil was first activated with DSP according to the method given in Example 1. The DSP activated gold was then reacted with ethylene diamine (20% v/v in isopropanol) at room temperature for 30 minutes. After incubation, the gold foil was rinsed thoroughly with isopropanol and then reacted with 0.1 M[1-ethyl-3-(3-dimethylaminopropyl) carbodiimide] in 20 mM phosphate buffer at pH 4.5, for 30 minutes at room temperature. The foil was then rinsed thoroughly with the phosphate buffer. Next, a solution of 10 mg/ml pepsin in phosphate buffer was added to the surface and allowed to incubate for 4 hours at 4° C. After incubation the foil was rinsed repeatedly with phosphate buffer and finally vacuum dried.

EXAMPLE 11

Au/pepsin Sample Presentation Surface Contacted with Pepsin

Figure 20:
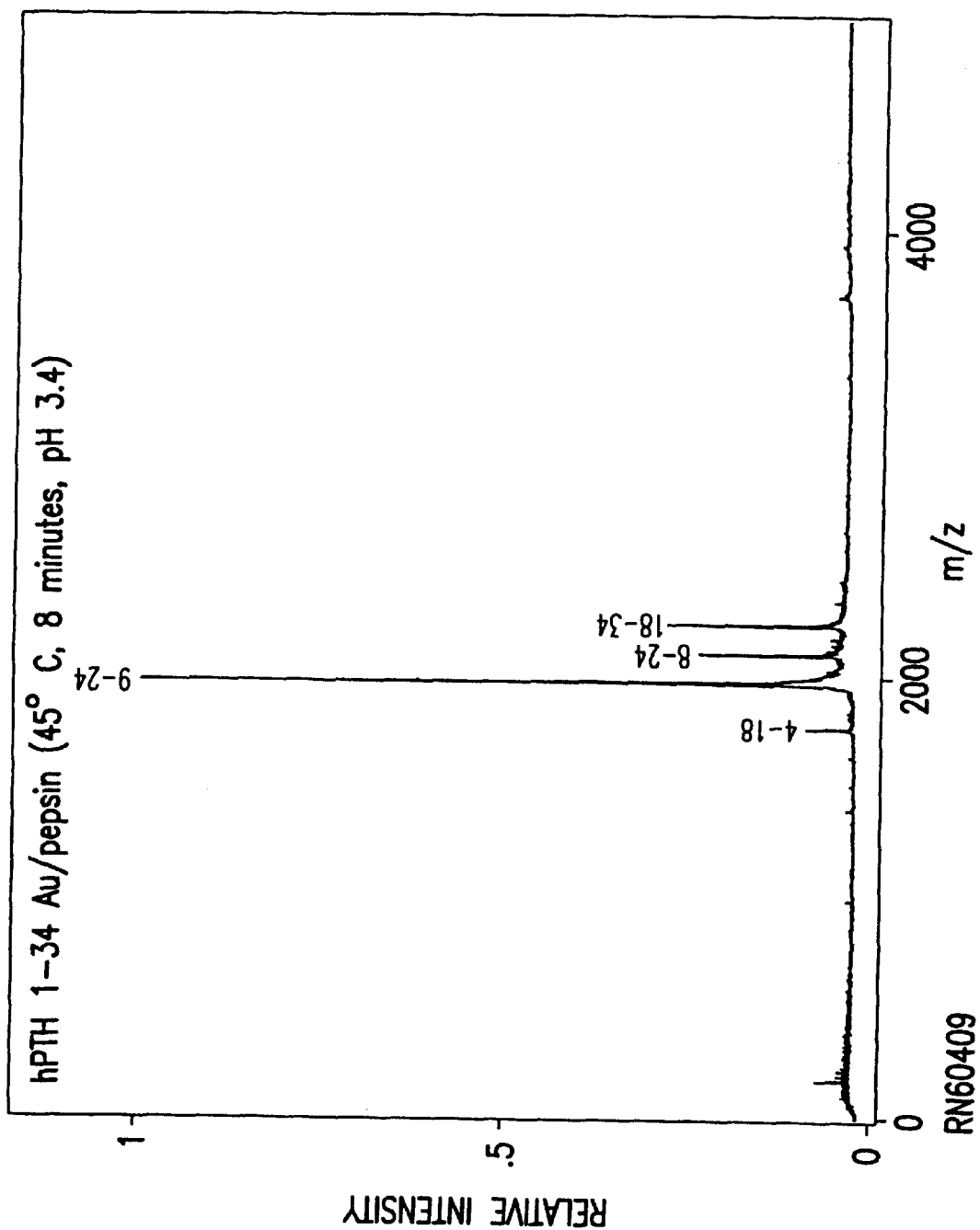
FIG. 20 is a MALDI mass spectrum of hPTH digested for 8 minutes on a surface-bound pepsin sample presentation apparatus maintained at 45° C., pH 3.4.

A digestion was performed with the Au/Pepsin active surfaces prepared in Example 10 by the application of approximately 5 pmole of hPTH 1–34 in 10 mM ammonium acetate buffer (pH 3.4). The hPTH was digested for 8 minutes at 45° C. before stopping the reaction by adding ACCA matrix. Time-of-Flight mass spectrometry was then performed. The resulting spectrum shown in FIG. 20 includes ion signals for the pepsin-generated peptides corresponding to amino acids 4–18, 9–24, 8–24, and 18–34.

EXAMPLE 12

Sequential Treatment of a Biomolecule By Two Different Complexes

The combination of two different surface bound complexes was used to modify a biomolecule in sequence as follows. First hPTH was digested for 10 minutes at 35° C., pH 8.1 using an immobilized Au/α-chymotrypsin sample presentation device as described in Example 2. A portion of the digest mixture was then transferred to a cpp activated apparatus prepared as described in Example 2 and the pH of the solution was adjusted to approximately 5. The cpp digestion was allowed to proceed for 10 minutes at 35° C. before termination by the addition of the ACCA matrix.

Figure 21:
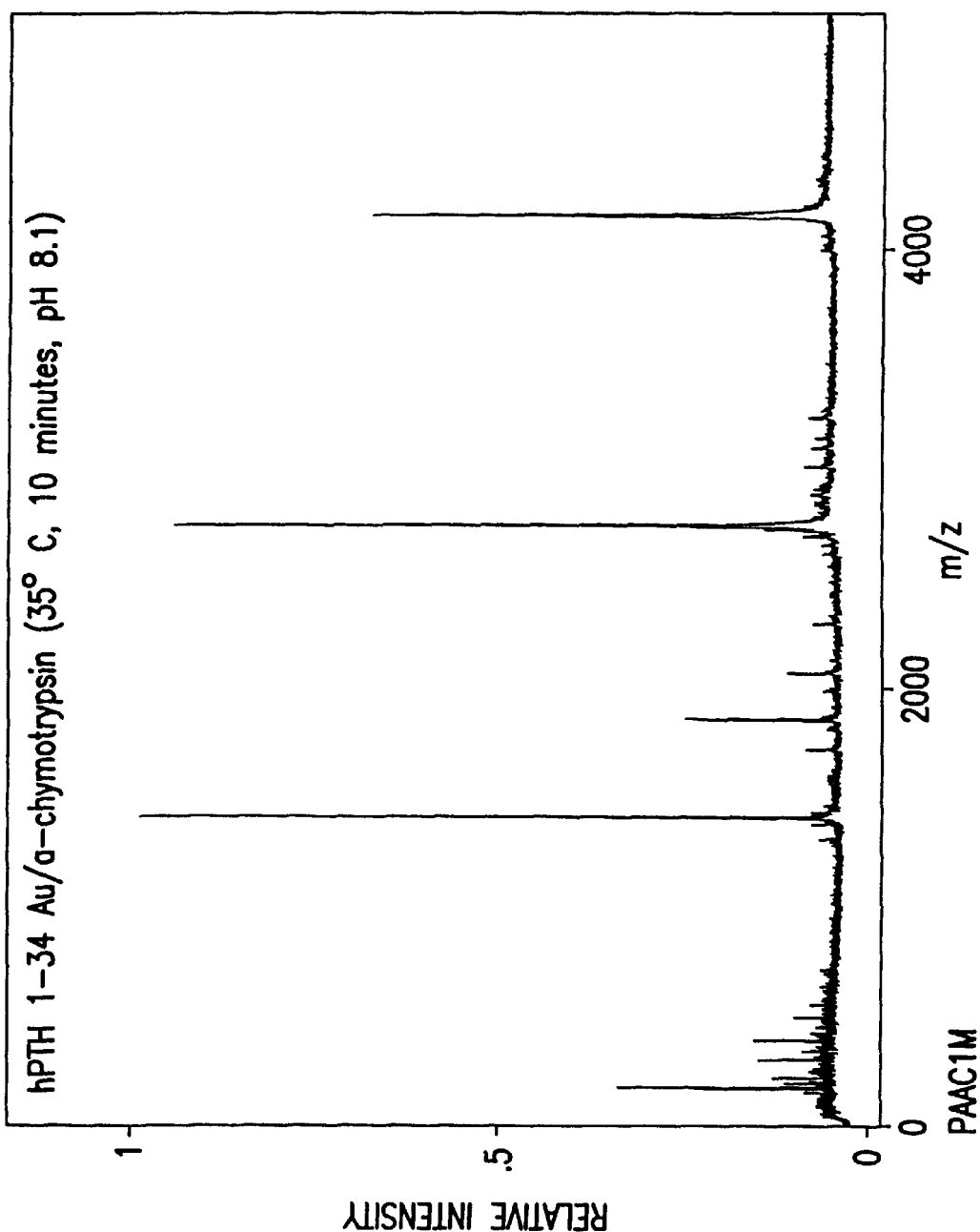
FIG. 21 is a MALDI mass spectrum of hPTH digested for 10 minutes on a surface-bound α-chymotrypsin mass sample presentation apparatus maintained at 45° C., pH 3.4.
Figure 22:
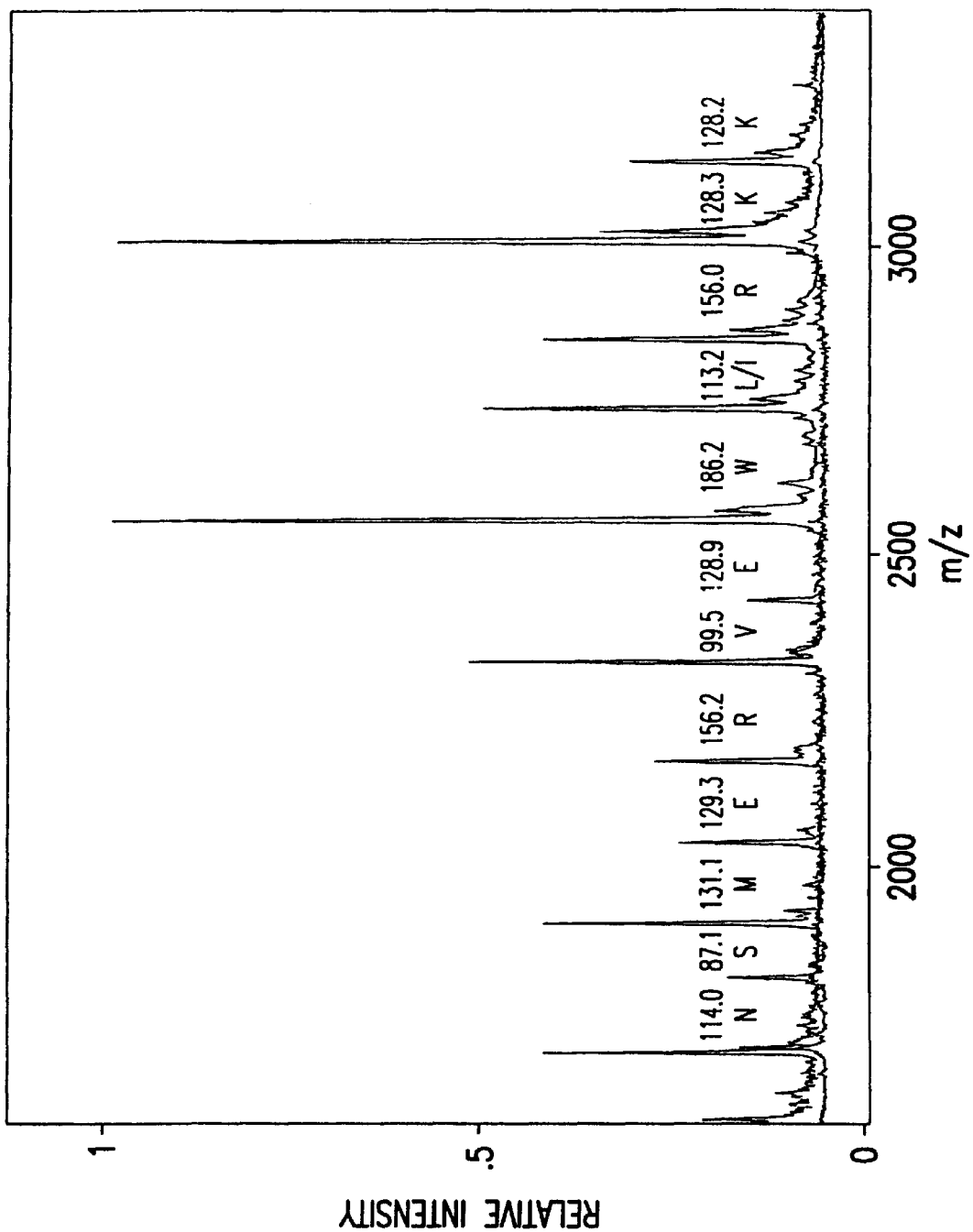
FIG. 22 is a MALDI mass spectrum of hPTH digested for 10 minutes on a surface-bound α-chymotrypsin mass sample presentation apparatus maintained at 45° C., pH 3.4, followed by a 10 minute digestion by surface-bound cpp maintained at 35° C., pH 5.

The mass spectrum of the results of the initial Au/α-chymotrypsin digestion is shown in FIG. 21. Ion signals resulting from the α-chymotrypsin cleavage of hPTH are observed. The mass spectrum of the results of the Au/cpp digestion of the α-chymotrypsin digestion mixture is shown in FIG. 22. New ion signals indicated by an asterisk "*" are observed. These new signals correspond to the C-terminal digestion of the original peptide species.

EXAMPLE 13

Purification of Biomolecules

The invention can be used to purify biomolecules as follows. For many biological studies, it is essential to remove undesirable proteases from biological solutions. Aprotinin is a single-chain basic 58-amino-acid polypeptide with a molecular mass of 6512 Daltons that has a polyvalent inhibitory action on proteases. Specifically, it inhibits a variety of enzymes belonging to the family of serine proteases by binding to the active site of the enzyme, forming tight complexes. A mass spectrometry sample presentation apparatus is prepared by tethering aprotinin to the surface in a manner similar to that described in Example 2. A solution of a polypeptide and a protease is added to the surface. The protease is removed from solution by the aprotinin. Mass spectrometry is performed and only the purified polypeptide should be observed.

EXAMPLE 14

Preparation of A Sample Presentation Apparatus Which Purifies Biomolecules By Ion Exchange An ion exchange functionality such as a diethylaminoethyl derivative, a t-butyl amino derivative (for anion exchange), a sulfite derivative, a carboxylic acid derivative (for cation exchange), or a combination of the above is immobilized to a sample presentation surface prepared according to Example 1.

EXAMPLE 15

Purification of Biomolecules By Ion Exchange

A biomolecule-containing solution is added to a surface prepared according to Example 14. The ion exchange functionality bound to the sample presentation surface exchanges ions with detrimental ionic species present as impurities in the biomolecule-containing solution.

EXAMPLE 16

Analysis of DNA Using Sample Presentation Apparatus

First, the nuclease, snake-venom phosphodiesterase, is attached to the sample presentation apparatus surface. This attachment may be accomplished using a tethering molecule in a manner similar to that described in Example 2. Second, DNA is added to the surface. After the phosphodiesterase has produced DNA fragments, a MALDI matrix is added, and MALDI time-of-flight mass spectrometry is performed.

EXAMPLE 17

Analysis of Carbohydrate Using Sample Presentation Apparatus

An enzyme such as mannase which digests carbohydrates is attached to the sample presentation apparatus surface. This attachment may be accomplished using a tethering molecule in a manner similar to that described in Example 2. Next, a carbohydrate is added to the surface. After the mannase has produced carbohydrate fragments, a MALDI matrix is added, and MALDI time-of-flight mass spectrometry is performed.

Many other variations and modifications of the invention will be apparent to those skilled in the art without departing from the spirit and scope of the invention. The above-described embodiments are, therefore intended to be merely exemplary, and all such variations and modifications are intended to be included within the scope of the claims.

We claim:

1. A mass spectrometer, which comprises a mass spectrometry sample presentation apparatus which comprises:
   (a) a mass spectrometry sample presentation surface, wherein the surface is a metal surface;
   (b) a complex immobilized on the sample presentation surface, the complex comprising (i) a tethering molecule selected from the group consisting of dithiothreitol, dimethyladipimidate-2*HCL, dimethylpimelimidate*HCL, dimethylsuberimidate*2HCL, dimethyl 3,3'-dithiobispropionimidate*2HCL, disuccinimidyl glutarate, disuccinimidyl suberate, bis (sulfosuccinimidyl) suberate, dithiobis (succinimidylpropionate), dithiobis (sulfosuccinimidylpropionate), ethylene glycobis (succinimidylsuccinate), ethylene glycobis (sulfosuccinimidylsuccinate), disuccinimidyl tartarate, disulfosuccinimidyl tartarate, bis [2-(succinimidyloxycarbonyloxy)ethyl] sulfone, bis [2-(sulfosuccinimidooxy-carbonyloxy)ethyl] sulfone, succinimidyl 4-(N-maleimido-matyl) cyclohexane-1-carboxylate, sulfo-succinimidyl 4-(N-maleimidomethyl) cyclohexane-1-carboxylate, m-Maleimidobenzoyl-N-hydroxysuccinimide ester, m-maleimidobenzoyl-N-hydroxysulfosuccinimide ester, succinimidyl 4-p-maleimido-phenyl)-butyrate, sulfosuccinimidyl 4-(p-maleimidophenyl)-butyrate, bismaleimidohexane, N-(λ-maleimidobutyryloxy) succinimide ester, N-(λ-maleimidobutyryloxy) sulfosuccinimide ester, n-succinimidyl (4-iodoacetyl) aminobenzoate, sulfosuccinimidyl (4-iodoacetyl)-aminobenzoate, 1,4-di-[3'-2'-pyridyldithio (propionamido) butane], 4-succinimidyl-oxycarbonyl-α(s-pyridyldithio) toluene, sulfosuccinimidyl-6-[α-methyl-α-(2-pyridyldithio)-toluamido] hexanoate, n-succinimidyl-3(2-pyridyldithio)-propionate, succinimidyl 6-[3-(2-pyridyldithio)-propionamido] hexanoate, sulfosuccinimidyl-6-[-3-(2-pyridyldithio)-propionamido] hexanoate, sulfosuccinimidyl-6-[3-(2-pyridyldithio)-propionamido] hexanoate, 3-(2-pyridyldithio)-propionyl hydrazine, 1-ethyl-3-(3-dimethylaminopropyl)-carbodiimide hydrochloride, n,n'-dicyclohexylcarbodiimide, 4-(p-azidosalicylamido)-butylamine, azidobenzoyl hydrazine, n-5-azido-2-nitrobenzoyloxysuccinimide, n-5-azido-2-nitrobenzoyloxysuccinimide, n-[4-(p-azidosalicylamido)butyl]-3'(2'-pyridyldithio) propionamide, p-azidophenyl glyoxal monohydrate, 4-(p-azidosalicyl-amido) butylamine, 1-(p-azidosalicylamido)-4-(iodoacetamido) butane, bis-[β-4-azidosalicylanido)ethyl] disulfide, n-hydroxysuccinimidyl-4-azidobenzoate, n-hydroxysulfo-succinimidyl 4-azidobenzoate, n-hydroxysuccinimidyl-4-azidosalicylic acid, n-hydroxysulfosuccinimidyl-4-azidosalicylic acid, sulfosuccinimidyl-(4azidosalicylamido)-hexanoate, p-nitrophenyl-2-diazo-3,3,3-trifluoropropionate, 2-diazo-3,3,3,-trifluoro-propionate, n-succinimidyl-(4-azidophenyl) 1,3'-dithiopropionate, sulfosuccinimidyl-(4-azidophenyldithio) propionate, sulfosuccinimidyl-2-(7-azido4-methylcoumarin-3-acetamide) ethyl-1,3'-dithiopropionate, sulfosuccinimidyl 7-azido4-methylcoumarin-3-acetate, sulfosuccinimidyl 2-(m-azido-o-nitrobenzamido)-ethyl-1,3'-dithiopropionate, n-succinimidyl-6-(4'-azido-2'-nitrophenyl-amino) hexanoate, sulfosuccinimidyl 6-(4'-azido-2'-nitrophenylamino) hexanoate, sulfosuccinimidyl 2-(p-azidosalicylamido) ethyl-1,3'-dithiopropionate, sulfosuccinimidyl 4-(p-azidophenyl)-butyrate and mixtures thereof, attached to the sample presentation surface, and (ii) at least one reactive molecule attached to the tethering molecule, wherein the reactive molecule digests a biomolecule upon contact thereby providing biomolecule fragments for analysis, and wherein the biomolecule is selected from the group consisting of polypeptides, DNA, carbohydrates, RNA and combinations thereof; and (c) a mixture of biomolecule fragments and MALDI matrix material on the sample presentation surface, the biomolecule fragments resulting from biomolecule digestion.

2. The mass spectrometer according to claim 1, wherein the metal surface is a gold surface, and wherein the tethering molecule is selected from the group consisting of dithiobis (succinimidylpropionate), dithiobis (sulfosuccinimidylpropionate), 1,4-di-[3'-2'-pyridyldithio (propionamido) butane], 4-succinimidyl-oxycarbonyl-α-(2-pyridyldithio) toluene, sulfosuccinimidyl-6-[α-methyl-α-(2-pyridyldithio)-toluamido] hexanoate, n-succinimidyl-3-(2-pyridyldithio)-propionate, succinimidyl-6-[3-(2-pyridyldithio)-propionamido] hexanoate, sulfosuccinimidyl-6-[-3-(2-pyridyldithio)-propionamido] hexanoate, sulfosuccinimidyl-6-[3-(2-pyridyldithio)-propionamido] hexanoate, 3-(2-pyridyldithio)-propionyl hydrazine, n-[4-(p-azidosalicylamido)butyl]-3'(2'-pyridyldithio) propionamide, p-azidophenyl glyoxal monohydrate, bis-[β-4-azidosalicylamido)ethyl] disulfide, n-succinimidyl-(4-azidophenyl) 1,3'-dithiopropionate, sulfosuccinimidyl-(4-azidophenyldithio) propionate, sulfosuccinimidyl-2-(7-azido-4-methylcoumarin-3-acetoamide) ethyl-1,3'-dithiopropionate, sulfosuccinimidyl 2-(m-azido-o-nitrobenzamido)-ethyl-1,3'-dithiopropionate, sulfosuccinimidyl 2-(p-azidosalicylamido) ethyl-1,3'-dithiopropionate, and mixtures thereof.

3. The mass spectrometer according to claim 1, wherein the biomolecule fragments are polypeptide fragments, and the reactive molecule is a proteolytic enzyme.

4. The mass spectrometer according to claim 3, wherein the proteolytic enzyme is selected from the group consisting of trypsin, α-chymotrypsin, pepsin and carboxypeptidase-P.

5. The sample presentation apparatus according to claim 1, wherein the biomolecule fragments are polypeptide fragments and the reactive molecule is a chemical cleavage agent having specificity for amino acid residues.

6. The mass spectrometer according to claim 1, wherein the biomolecule fragments are DNA or RNA fragments, and the reactive molecule is an endonuclease or exonuclease.

7. A spectrometer according to claim 1, which further comprises:
(a) means for introducing a sample presentation surface into a volatilization chamber;
(b) means for volatilizing and ionizing the biomolecule fragments, thereby forming biomolecule fragment ions, said means for volatilizing comprising (i) a matrix material which solubilizes the biomolecule fragments and absorbs light energy at a frequency easily accessible by a laser, wherein the matrix material is applied over the complex, and (ii) means for volatilizing the matrix material; and
(c) means for determining a molecular weight to charge ratio of the biomolecule fragment ions based on trajectory.

8. A mass spectrometer according to claim 7, wherein the mass spectrometer further comprises means for generating an electric field, the field being oriented to cause the biomolecule fragment ions to travel away from the sample presentation apparatus and toward a detecting means.

9. A mass spectrometer according to claim 7, wherein the means for volatilizing the matrix material is a LASER.

10. A mass spectrometer according to claim 9, wherein the means for determining the molecular weight to charge ratio of the biomolecule fragments measures the time of flight for the biomolecule fragments.

* * * * *

UNITED STATES PATENT AND TRADEMARK OFFICE
CERTIFICATE OF CORRECTION

PATENT NO.    : 6,093,541
DATED         : July 25, 2000
INVENTOR(S)   : Nelson

It is certified that error appears in the above-identified patent and that said Letters Patent is hereby corrected as shown below:

Column 10,
Line 65, "a-cyano-4-" should read -- α-cyano-4- --
Line 67, "aci-" should be deleted Column 11,
Line 1, "d:acetonitrile" should read -- acid:acetonitrile --

Column 14,
Line 67, "Au/a-chymotrypsin" should read -- Au/α-chymotrypsin --

Column 20,
Line 21, "sample presentation apparatus" should read -- mass spectrometer --.

Signed and Sealed this

Ninth Day of April, 2002

Attest:

*Attesting Officer*

JAMES E. ROGAN
*Director of the United States Patent and Trademark Office*